United States Patent
Nosé et al.

(10) Patent No.: US 8,926,543 B2
(45) Date of Patent: Jan. 6, 2015

(54) IMMUNOACTIVATION BLOOD PERFUSION FILTER FOR THE TREATMENT OF MALIGNANT TUMORS

(75) Inventors: Yukihiko Nosé, Houston, TX (US); Ako Nosé, legal representative, Houston, TX (US); Kazuhide Ohta, Osaka (JP); Hiroshi Miyamoto, Tokushima (JP); Junji Takaba, Osaka (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/394,765

(22) PCT Filed: Oct. 7, 2010

(86) PCT No.: PCT/US2010/051832
§ 371 (c)(1),
(2), (4) Date: Aug. 23, 2012

(87) PCT Pub. No.: WO2011/044369
PCT Pub. Date: Apr. 14, 2011

(65) Prior Publication Data
US 2013/0046225 A1 Feb. 21, 2013

Related U.S. Application Data

(60) Provisional application No. 61/249,867, filed on Oct. 8, 2009.

(51) Int. Cl.
*A61M 1/16* (2006.01)
(Continued)

(52) U.S. Cl.
CPC .......... *A61K 31/727* (2013.01); *A61M 1/3621* (2013.01); *A61M 1/16* (2013.01);
(Continued)

(58) Field of Classification Search
CPC .......... A61M 1/3627; A61M 1/3633; A61M 1/3621; A61M 1/3666; A61M 1/367; A61M 1/14; A61M 1/16; A61M 2001/3621; A61M 2001/3687; A61M 2205/75; A61M 2210/12; A61M 1/3496; B01J 20/00

USPC .......... 604/6.07, 4.01, 5.02, 5.04, 6.01, 6.03, 604/6.09, 6.1, 6.11, 6.13, 6.14, 6.15, 6.16; 210/645

See application file for complete search history.

(56) References Cited

U.S. PATENT DOCUMENTS

| 4,130,642 A | 12/1978 | Kikugawa et al. |
| 4,445,500 A | 5/1984 | Osterholm |

(Continued)

FOREIGN PATENT DOCUMENTS

| EP | 2 058 018 A1 | 5/2009 |
| JP | 53-59017 A | 5/1978 |

(Continued)

OTHER PUBLICATIONS

"Membrane biocompatibility does not affect whole body protein metabolism during dialysis." Jorden M Veeneman et al. Blood Purification Feb. 2005; 23(3):211-8. DOI:10.1159/000084891 http://www.researchgate.net/publication/7925895_Membrane_biocompatibility_does_not_affect_whole_body_protein_metabolism_during_dialysis. accessed Jun. 12, 2013.*

(Continued)

*Primary Examiner* — Adam Marcetich
(74) *Attorney, Agent, or Firm* — Finnegan Henderson Farabow Garrett & Dunner LLP

(57) ABSTRACT

The invention provides a way of producing a natural immunologically active state in a person by subjecting him to an apheresis procedure with bioincompatible biomaterials for about one hour. To safely control the immunological shock induced by this procedure, the person is put under general anesthesia for about six hours, including the apheresis time and at least an additional five hours thereafter. This immunological activation is useful for treating malignant tumors and diseases related to immunosuppression, such as AIDS. The invention also provides for the use of an apheresis column containing a blood perfusion filter with bioincompatible materials for treating malignant tumors and infectious diseases.

19 Claims, 32 Drawing Sheets

ONE UNIT OF FILTER CHAMBER UNIT

PVA (NON-WOVEN) (2) 2mm THICK
1g OF WELL WASHED NON-SYNTHETIC FIBERS OF LESS THAN 5μm DIAMETER (POSSIBLY 1-2μm) SPREAD EVENLY

5 UNITS OF FIBER CHAMBER (5g OF FIBER MATERIAL) STORED IN 4% FORMALDEHYDE

(51) Int. Cl.
  *A61M 1/36* (2006.01)
  *A61K 31/727* (2006.01)
  *A61M 1/14* (2006.01)
  *A61K 31/135* (2006.01)
  *A61M 1/34* (2006.01)
  *B01J 20/00* (2006.01)
  *B01D 15/00* (2006.01)
  *B01J 20/22* (2006.01)

(52) U.S. Cl.
  CPC ............. *A61M 1/14* (2013.01); *A61K 31/135* (2013.01); *A61M 1/3496* (2013.01); *B01J 20/00* (2013.01); *A61M 1/3486* (2014.02); *B01D 15/00* (2013.01); *B01J 20/22* (2013.01); *B01J 2220/4825* (2013.01); *B01J 2220/4831* (2013.01)
  USPC ....... 604/6.09; 604/4.01; 604/5.02; 604/5.04; 604/6.01

(56) References Cited

U.S. PATENT DOCUMENTS

| | | | |
|---|---|---|---|
| 5,476,444 A * | 12/1995 | Keeling et al. | 604/6.13 |
| 5,498,336 A * | 3/1996 | Katsurada et al. | 210/496 |
| 5,677,176 A | 10/1997 | Nicolau et al. | |
| 6,264,680 B1 * | 7/2001 | Ash | 607/106 |
| 6,498,007 B1 * | 12/2002 | Adachi et al. | 435/5 |
| 6,827,898 B1 * | 12/2004 | Fausset et al. | 422/46 |
| 8,496,833 B2 | 7/2013 | Kobayashi | |
| 2001/0039441 A1 * | 11/2001 | Ash | 607/106 |
| 2002/0033181 A1 * | 3/2002 | Groth et al. | 128/898 |
| 2003/0062299 A1 | 4/2003 | Lee et al. | |
| 2004/0006214 A1 * | 1/2004 | Ogino et al. | 530/388.3 |
| 2004/0055609 A1 * | 3/2004 | Groth et al. | 128/898 |
| 2005/0014127 A1 * | 1/2005 | Onodera et al. | 435/2 |
| 2005/0145573 A1 * | 7/2005 | Nanko et al. | 210/690 |
| 2005/0187508 A1 * | 8/2005 | Gorsuch et al. | 604/6.04 |
| 2007/0190050 A1 * | 8/2007 | Davidner et al. | 424/140.1 |
| 2009/0060890 A1 * | 3/2009 | Humes et al. | 424/93.71 |
| 2009/0234266 A1 * | 9/2009 | Solomon et al. | 604/6.09 |
| 2009/0275874 A1 * | 11/2009 | Shimagaki et al. | 604/6.03 |

FOREIGN PATENT DOCUMENTS

| | | |
|---|---|---|
| JP | 01-124382 A | 5/1989 |
| JP | 2005-304647 A | 11/2005 |
| WO | WO 20061073106 A1 | 7/2006 |

OTHER PUBLICATIONS

"Selected Indicators of Food and Agriculture Development in Asia-Pacific Region 1992-2002." Food and Agriculture Organization of the United Nations Regional Office for Asia and the Pacific, Bangkok. Oct. 2003. ftp://ftp.fao.org/docrep/fao/004/ad452e/ accessed Jun. 20, 2013.*

Robinson, William R.; Nash, John J. "Half Lives." Visualization and Problem Solving for General Chemistry. http://www.chem.purdue.edu/gchelp/howtosolveit/Kinetics/Halflife.html Accessed Jan. 24, 2014.*

Yukihiko Noséet al. "Membrane Apheresis Technology: Historical Perspective and New Trends toward Biocompatible Systems." DOI: 10.1111/j.1744-9987.1997.tb00005.x Therapeutic Apheresis vol. 1, Issue 1, pp. 5-12, Feb. 1997.*

Yukihiko Nosé. "Biocompatible Biomaterials for Extracorporeal Immunomodulation." DOI: 10.1111/j.1525-1594.1988.tb02790.x Artificial Organs vol. 12, Issue 5, pp. 377-378, Oct. 1988.*

International Search Report from the United States Patent and Trademark Office for International Application No. PCT/US2010/051832, mailed Dec. 1, 2010.

Written Opinion of the International Searching Authority from the United States Patent and Trademark Office for International Application No. PCT/US2010/051832, mailed Dec. 1, 2010.

Yonekawa et al.; "Extracorporeal Granulocytapheresis for Cancer and Rheumatoid Arthritis", Transfusion Science, vol. 17, No. 3, pp. 463-472, (1996).

Mojcik et al.; "Aprotinin and the Systemic Inflammatory Response After Cardiopulmonary Bypass", The Annals of Thoracic Surgery, vol. 71, pp. 745-754, (2001).

* cited by examiner

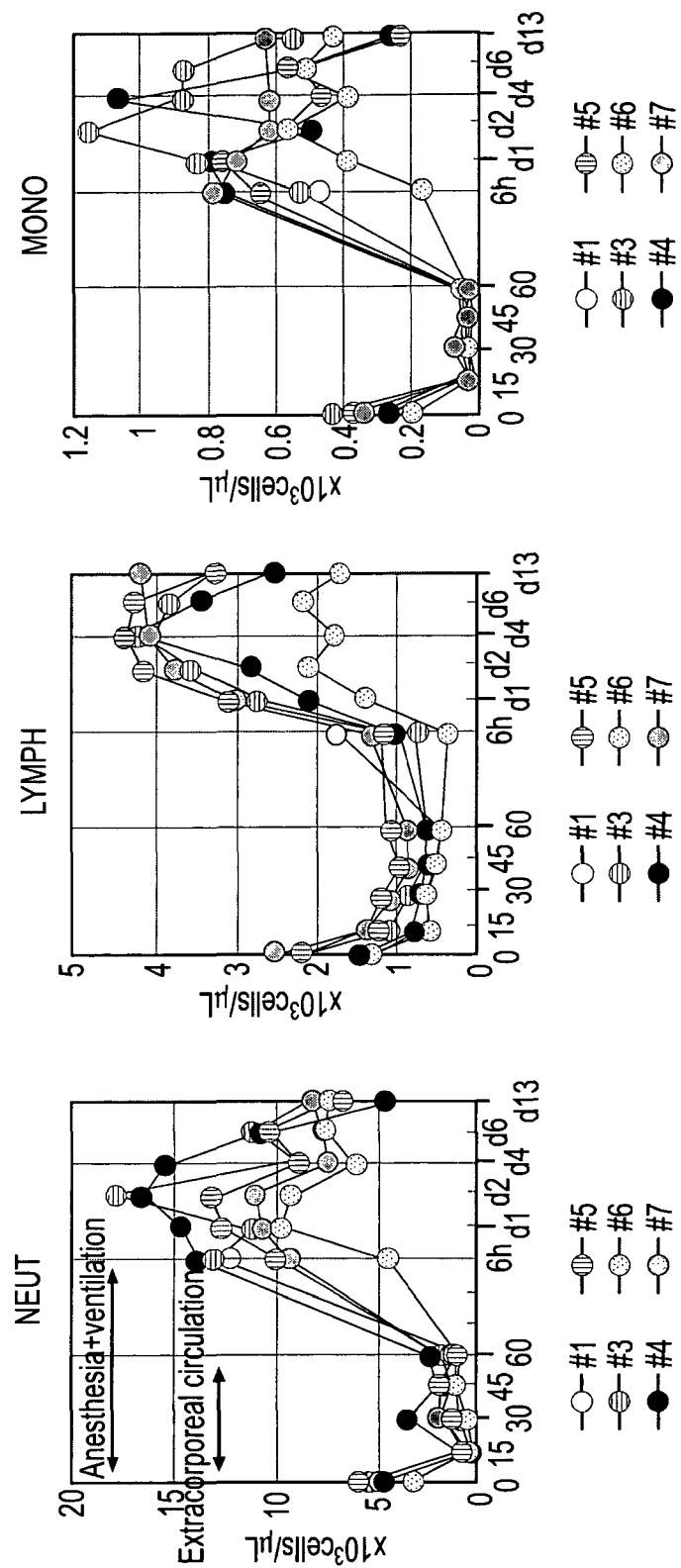

IMMUNOACTIVATION BLOOD PERFUSION FILTER FOR THE TREATMENT OF MALIGNANT TUMORS

CROSS REFERENCE TO RELATED APPLICATIONS

This application is based on and claims the benefit of U.S. Provisional Application No. 61/249,867, filed Oct. 8, 2009. The entire disclosure of this provisional application is relied upon and incorporated by reference herein.

INTRODUCTION

Malignant tumors can develop in patients who are immunologically suppressed. A large number of malignant tumor cells are produced inside the body every day. Fortunately, the immune system recognizes them as "not normal" or "non-self" cells and subsequently destroys them every day. Therefore, if the immune system functions properly, the chances of developing cancer are reduced.

The immune system can be activated via vaccination. However, the resulting attack on cancer cells by the patient's own immune system is not strong enough when vaccines are used. More effective and stronger immunogical challenges are required to be able to destroy malignant tumor cells, which the patient's immune system has not recognized as the cells to destroy. As a result, the treatment of malignant tumors involves not only surgical removal of the primary foci of the tumor, but also drug and radiation therapies to destroy throughout the body possible metastatic tumor cells. Unfortunately, anticancer drug therapies introduce various types of unpleasant side effects that can often necessitate interruption of drug therapies before achieving effective therapeutic outcomes.

In the past, apheresis therapies to suppress a patient's immune system have been used to treat autoimmune diseases. For these types of patients, removal of pathological molecules in the blood causing autoimmune diseases demonstrated therapeutic effects. For these types of patients, humoral factors such as auto-antibodies, immunocomplexes, cytokines, and activated complement were removed via apheresis as well as cellular factors, such as leukocytes. This type of therapy created an immunologically suppressed state in the patient, which is exactly the opposite effect on the immune system that is needed to treat a cancer patient.

SUMMARY OF THE INVENTION

The invention provides a way to strongly activate a person's immune system by using an extracorporeal blood perfusion filter that is present in an apheresis column. The resulting immunoactivation leads to the destruction of malignant tumor cells via apoptosis. The method of the invention, however, causes substantial physiological impacts on the person including transient low blood pressure and hypoxia. To manage these impacts, the extracorporeal apheresis is conducted with the person under general anesthesia. The general anesthesia, along with careful blood pressure and oxygen saturation monitoring, assures the safe activation of the person's immune system and eliminates any discomfort associated with this procedure. The general anesthesia is administered not only during the apheresis procedure but also during intracorporeal immunoactive modulation period of 6 hours.

It is possible to introduce immunostimulation using a perfusion filter with bioincompatible materials. Perfusion of patients' blood through an apheresis column containing such a filter for one hour at the rate of approximately 100 ml/min, can generate such condition. The method of the invention leads to immunoactivation during the initial 30 minutes of extracorporeal circulation. This molecular surgery procedure for treating a malignant tumor by immnoactivation leads to direct and controllable effects in the first 30 minutes with a return to normal in several hours. These effects include hypotension (approximately 50% reduction in blood pressure), leukocytopenia (approximately a 70% reduction in leukocytes), and respiratory difficulty resulting in hypoxia with the lowest blood oxygen levels occurring 30 minutes after the procedure begins.

These effects are reversible by reducing blood flow through the apheresis column and by providing physiological support to the person. Such support includes general anesthesia with endothracheal tube, blood pressure control (continuous monitoring of the blood pressure), and oxygen supply control (continuous monitoring of blood oxygen saturation).

Because of the transient shock syndrome induced by immunoactivation apheresis systems, no specific immunoactivation columns were provided or applied clinically in the past. The United States Food and Drug Administration has classified such apheresis systems as clinically unsafe because of the shock symptoms associated with their use. The method of the invention overcomes this problem, by providing a way to powerfully activate the immune system while simultaneously controlling the shock symptoms that accompany the use of a blood perfusion filter according to the invention.

The controlled immunological shock, induced by the bioincompatible material present in the blood perfusion filter of the invention, produces an immunoactive status on experimental animals. To provide a safe, painless, effective, and reproducible therapeutic result, general anesthesia with endotracheal intubation is provided not only during the one-hour apheresis procedure but also for an additional five hours. No animal treated with this procedure died during animal experiments, nor were there any procedurally related physical or sensual abnormalities demonstrated.

Providing general anesthesia for about six hours includes not only the initial 30 minutes of the hypotension and hypoxic stages of shock, but also the recovery stages in which the animals become hemodynamically normalized. After six hours, accumulated leukocytes in the lung are released back to the systemic circulation. During the initial stages of apheresis, granulocytes decrease almost 100% while lymphocytes decrease only 40-50%, this creating a transient lymphocyte dominant state in the person's immune system. During the six hours of general anesthesia, immunostimulatory cytokines TNF-α and IL-6 can increase up to 1,000 fold. After the 6 hours, leukocyte counts in the blood return almost back to pre-procedure levels, and later increases further. After 4 days, leukocyte counts more than double compared to pre-procedure levels. Cellular and humoral activation then normalize after two weeks.

The induced immunostimulation provided by the method of the invention can have therapeutic effects for treating malignant tumors and for treating incurable infectious diseases including acquired immunodeficiency syndrome (AIDS).

BRIEF DESCRIPTION OF THE DRAWINGS

FIG. 23 shows the kinetics of lymphocyte, neutrophil, and monocyte recovery in dogs during and after perfusion according to one embodiment of the invention. The Y axis measures the number of each cell type present in whole blood at each time point.

DETAILED DESCRIPTION OF THE INVENTION

Figure 1:
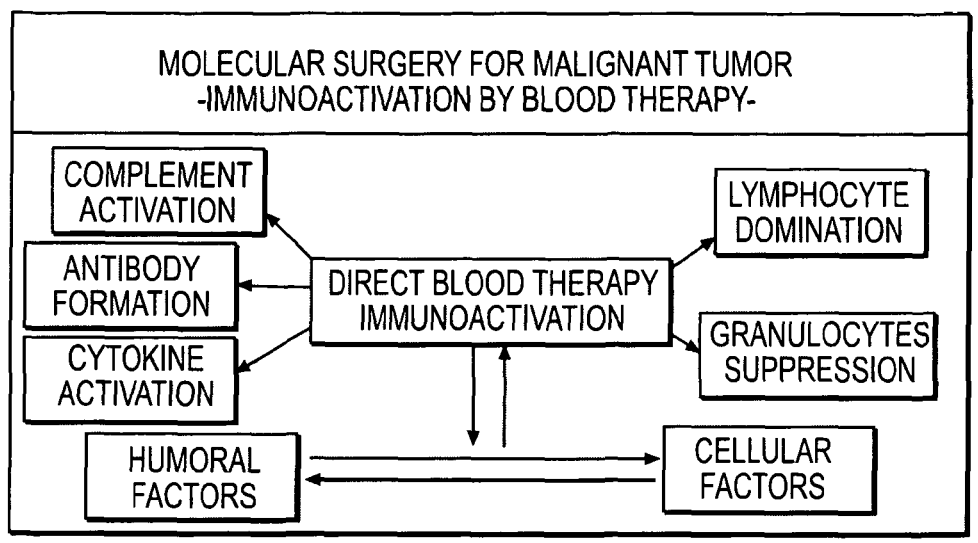
FIG. 1 provides a schematic of the immunoactivation effects that occur in the patient as a result of the apheresis method of the invention. Not only are humoral factors activated, but also cellular factors are activated.

As discussed above, a large number of malignant tumor cells are produced inside a person's body every day. Fortunately the immune system recognizes them as abnormal cells and destroys them every day. If the immune system is functioning properly, the chances of developing cancer are minimized. Unfortunately, if a person's immune system is suppressed, the cancer cells will not be recognized as the foreign cells to be destroyed. In this situation, cancer cells are left alone in a malignant tumor growing unchecked in the host.

To develop a therapeutic treatment for malignant tumors, the invention provides a safe, effective, and reproducible method of producing immunologically active state of the patient. In one embodiment, the patient is a human patient. In another embodiment, the patient is a non-human animal in which case the invention may be used in veterinary setting. Non-human animals include, but are not limited to, cats, dogs, cattle, and horses. Currently, it is possible to suppress the immunological status of patients by blood purification (apheresis). Removal of the plasma factors and/or cellular factors responsible for maintaining the active state of a person's immune system state is possible by apheresis. See Nosé 1995. This method of blood purification was introduced for the treatment of autoimmune disease patients. In the past, apheresis procedures were introduced to treat autoimmune diseases such as rheumatoid arthritis or ulcerative colitis. Conversely, the removal of many molecular and cellular factors causing immunological suppression from a cancer patient was attempted, but the therapeutic effects of this apheresis did not reveal any positive outcomes for patients with malignant tumors. See Tani 1998.

Indeed, as shown in Table 1, effective therapy for treating a malignant tumor involves activation of the immune system, not suppression of the immune system. Thus, immunosuppressive apheresis techniques were not successful in treating malignant tumors. When a person is healthy and has a normal immune system, cancer cells are destroyed and tumors do not form. When the immune system is suppressed, cancer cells gain the opportunity to replicate in the body resulting in cancer for the person. When the person's immune system is chronically overstimulated, then autoimmune disease can result. Thus, in the case of cancer, successful therapy involves stimulation of a suppressed immune system.

TABLE 1

|  | Normal Cells | Foreign body & Abnormal Cells | Diseases | Cancer Therapy | Autoimmunological Disease Therapy |
|---|---|---|---|---|---|
| Activation of Immunological System | Destroyed | Destroyed | Autoimmune Disease |  |  |
| Normal | Maintained | Destroyed | Healthy |  |  |
| Suppressed Immunological System | Maintained | Maintained | Cancer Infection |  |  |

Based on the above rationale, treatment of a malignant tumor involves the enhancement of immunological function in a person to reach normal levels. As a result, the treated person's body regains the ability to recognize the cancer cells as abnormal cells and the malignant cells are destroyed by the person's normalized immune system. Such enhancement of immune function can be used to treat any disease associated with immune suppression including cancers and infectious diseases, such as bacterial, fungal, or viral infections. In one embodiment, the cancer manifests as one or more solid tumors in the body. In another embodiment, the cancer does not manifest as a solid tumor, for example in the case of leukemia. In one embodiment the viral infection can be a Human Immunodeficiency Virus (HIV) infection or a hepatitis virus infection such as Hepatitis A Virus (HAV), Hepatitis B Virus (HBV) or Hepatitis C Virus (HCV).

The invention provides a method of therapy by activating the suppressed immunological status of a patient using an apheresis technique. The Bacille Calmette Guerin (BCG) vaccine has been used to provide immunological activation against tuberculosis bacteria (Grange 2009). Unfortunately, effects of BCG were very small. The invention provides a more effective method of stimulating a patient's immune function making it more effective for the treatment of diseases associated with immunosuppression or infectious diseases.

The apheresis technique of the invention uses a blood perfusion filter comprising a bioincompatible material. As used herein, a "bioincompatible material" is a material that triggers a reaction from the body, whether it is an immunological reaction or a physiological reaction such as formation of an antibody as a result of exposure to the body either directly (e.g., introduction into the body) or indirectly (e.g., via extracorporeal circulation). Membrane-based blood purification systems had been developed for the treatment of autoimmune diseases. See Nosé 2000. For these blood purification apheresis systems, those in the art used filters made of blood compatible materials to avoid activation of the patient's immune system even though these systems removed cellular and molecular factors underlying autoimmune diseases.

In cases where bioincompatible apheresis filters result in immunoactivation, patients have to suffer many side effects including hypotension, respiratory failures, nausea, vomiting, excessive sweating, chills, and shivering. As used herein, "immunoactivation" or "activation of the immune system" refers to an increase in the number and/or function of cells of the immune system, such as lymphocytes, and/or an increase in the humoral function of the immune system relating to B cells and antibody production together with cytokine generation. In one embodiment, such cytokine generation can be the production of TNF-α and/or IL-6. In light of these side effects, government agencies, including the FDA in the US and the Ministry of Health and Welfare in Japan, prohibited the clinical application of such apheresis filters. As a consequence, such bioincompatible apheresis filters to introduce effective immunoactivation for the treatment of malignant tumors were not clinically approved.

The invention provides a method of therapy by activating the suppressed immunological status of a patient using bioincompatible materials in an apheresis technique. While side effects, such as hypotension and hypoxia, may occur during this technique, the invention provides a way of activating the immune system in a safe and controlled manner. As noted above, techniques other than apheresis, such as the BCG vaccine, have been used to provide immunological activation against tuberculosis bacteria (Grange 2009). Unfortunately, effects of BCG were very small. The invention provides a more effective method of stimulating a patient's immune function making it more effective for the treatment of diseases associated with immunosuppression or infectious diseases.

Other groups have used cellulose acetate to stimulate the immune system in cancer patients (Yonekawa 1997). Dr. Yonekawa utilized the cellulose acetate bead (Japanese Antibody Research Institute) columns for the cancer treatments (Yonekawa 1992). In 8 out of 9 patients, subjective symptoms, such as pain and fatigue, were improved. However, the effectiveness of this cellulose acetate bead column filter required a substantial number of treatments and even then did not yield clear results. More immunoactivation was required by more bioincompatible filters for a more effective treatment of cancer patients.

Another group has used Immugard R (Terumo Co., Japan) and a Cellsorba column by ASAHI Kasei Medical Co., Ltd. to treat ulcerative colitis. Compared with ASAHI filters, the Terumo filter demonstrated better clinical outcomes for the treatment of ulcerative colitis. The cellsorba column utilizes polyester fiber.

There are two additional apheresis columns that were used in an attempt to treat malignant tumors of the lungs and GI tract. The first column, known as Imugard, which is produced by Terumo Co. of Japan, experimentally contained cotton fibers from the *Gossypium barbadense* plant (Amano 1996). When this column was used for apheresis, patients experienced transient hypotension, a transient reduction of leukocytes, and activation of complement. At the onset of the extracorporeal circulation, transient hypotension occurred together with transient reduction of leukocytes. Complement activation also occurred quite substantially. Because of complications, the FDA did not approve the use of the column for clinical use. Terumo then tried to reduce the filter's bioincompatibility by switching the fiber from cotton fibers to synthetic fibers. In doing so, however, the column lost its effectiveness for the treatment of infection and for malignant tumors but still retained effectiveness for rheumatoid arthritis (Amano 1996). In essence, the Terumo column changed from an immunoactivation column into an immunosuppressive column when the filter's bioincompatibility was reduced. Currently Terumo utilizes the polyurethane filter and their Immugard is primarily used for removal of leukocytes for blood transfusion.

The second column contains purified *Staphylococcus aureus* Protein A, which has a high affinity for immune-complexed IgG antibodies. When this column was used for apheresis, patients experienced transient hypotension and chills. The similar experiences were obtained by the protein A column. This column had also been tried for cancer therapy (Messerschmidt 1998 and Ainsworth 1988). However, complications, such as hypotension and chill at the onset of extracorporeal circulation, occurred as with Terumo columns. So the FDA again insisted that the Protein A column should be made more biocompatible. After the manufacturer of the protein A column successfully improved its biocompatibility, the protein A column ceased to function for the treatment of malignant tumor but remained a treatment for rheumatoid arthritis (Levy 2003).

In cases where the immune system was activated by these bioincompatible apheresis filters, patients suffered many side effects including hypotension, respiratory failures, nausea, vomiting, excessive sweating, chills, and shiver. It was natural for government agencies, including the FDA in the U.S. and the Ministry of Health and Welfare in Japan, to prohibit clinical application of such apheresis filters. As a consequence, such bioincompatible apheresis filters to introduce effective immunoactivation for the treatment of malignant tumors were not clinically approved. In each case, however, when biocompatibilities were improved, the effects on malignant tumors disappeared. Thus, in the process of reducing these side effects, the Imugard column lost its effectiveness on tumor cells and instead remained effective for treating rheumatoid arthritis or ulcerative colitis. Similarly, the Protein A column also lost its effectiveness against tumor cells when it was modified to reduce side effects instead becoming effective for treating rheumatoid arthritis. Both rheumatoid arthritis and ulcerative colitis are conditions associated with an overactive immune response, demonstrating that the modified columns acted to suppress the patient's immune system.

In sum, when an apheresis column is modified to reduce its bioincompatiblity, the resulting column acts to suppress the patient's immune system by removal of autoantibodies (especially of the IgG3 subtype), removal of immunocomplexes, and/or removal of immunostimulatory cytokines. In contrast, apheresis columns containing bioincompatible material act to stimulate the immune system by increasing antibody production, increasing cytokine production, and skewing the leukocyte population in the patient's blood towards a lymphocyte dominant state.

To provide a clinically effective therapeutic method for treating malignant tumors and infectious diseases, the invention induces a controlled shock state in patients. In other words, the invention provides a way of using bioincompatible materials in an apheresis column to induce a temporary but powerful stimulation of the immune system while at the same time controlling the side effects that can accompany such stimulation. In the absence of providing such strong immunological stimulation, the immune system's ability to kill tumor cells via apoptosis is reduced. Currently provided apheresis without any cardiovascular protection is not acceptable for clinical use. The side effects associated with inducing immunological shock can be controlled by using general anesthesia. In this way, the invention provides a type of molecular surgery in which the patient's immune system is changed at the molecular level to hunt down and kill diseases-causing cells.

The differences of classical surgery conducted in the $20^{th}$ century and the molecular surgery proposed in the $21^{st}$ century are summarized in Table 2.

TABLE 2

|  | Classical Surgery $20^{th}$ Century | Molecular Surgery ($21^{st}$ Century) |
| --- | --- | --- |
| Removal tool | knife and scissors | membrane fibers and granules |
| Removal objectives | malignant and/or damaged tissues | blood cellular and humoral molecules |
| Procedures | cut and suture | extracorporeal blood therapy |
| Outcome | regeneration of new tissues | immunoactivation or immunosuppression |
| Anesthesia | general or local | general |

Surgical procedures in the $20^{th}$ century involve removing tissues by scissors and knife under general anesthesia. Blood purification procedures in the $21^{st}$ century remove molecular and cellular components by blood purification filters (apheresis) under general anesthesia. For this molecular method of cancer therapy, there are no complications or side effects that are commonly associated with radiation therapy or chemotherapies currently used for cancer therapy. There is no need to damage normal cells of the patient but only destroy abnormal malignant tumor cells. At the same time, it is very difficult to detect small metastatic regions to apply effective radiation therapies. In short, at this time there aren't any effective therapeutic regimens for the treatment of malignant tumors. Thus, in the 21$^{st}$ century, the therapeutic procedures for cancer should be molecular surgery with general anesthesia.

In the past, clinical apheresis procedures were performed on humans without general anesthesia. However, experimental apheresis procedures on dogs were performed with general anesthesia not for controlling the side effects of immunological shock, but for keeping the animals still during the procedure. As a result, general anesthesia was employed for a short period of time during the apheresis procedure itself. In contrast, the invention uses general anesthesia during two phases of physiological insults to the patient: (1) induction of immunoactivation by apheresis using a bioincompatible blood pheresis filter during the first hour and (2) safe maintenance of the transient lymphocyte-dominant immunoactive clinical stage during the subsequent 5 hours for tumor killing by cellular and humoral agents. Some experimental filters were bioincompatible and introduced such hemodynamic and respiratory changes, but there were no fatal incidents. However, these filters were not intended to enhance immunoactive state but instead aimed to suppress immunological activities.

The method of the invention results in the immunological modulations shown in FIG. 1 after about one hour of apheresis using the apheresis column of the invention. All of these phenomena are due to the immunoactivation of not only humoral factors but also cellular factors. In other words, it is the induced immunological shock as the result of the direct contact of the patient's blood to the bioincompatible biomaterials and subsequent phase 1 modulation (discussed below) of autoimmunological cellular and humoral adjustment of the patient intra-corporeally during this period of times of 6 hours. In one embodiment, the immunoactivation process is completed in two weeks.

Figure 2:
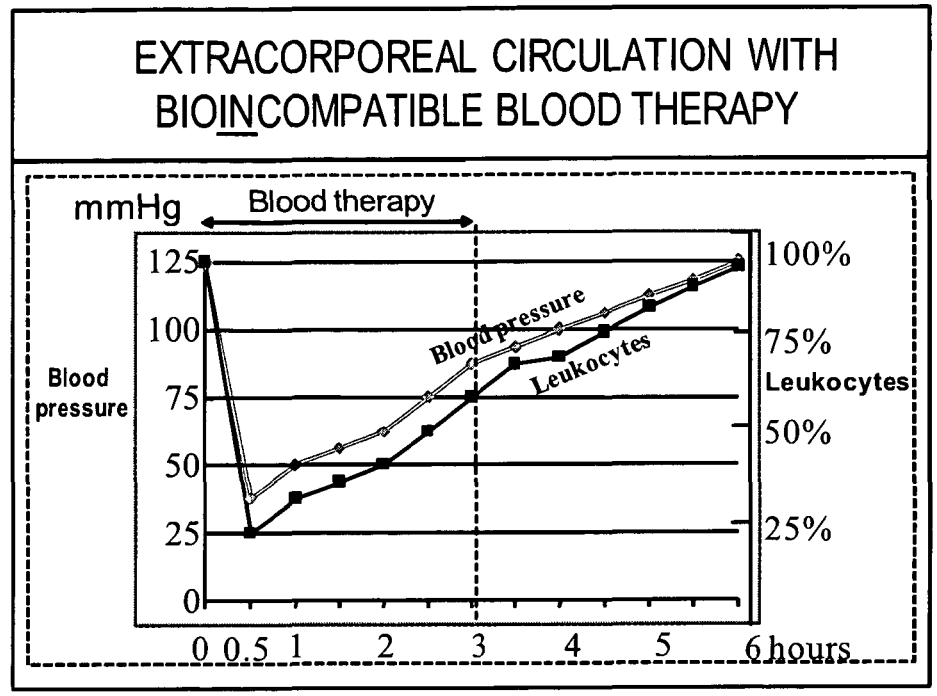
FIG. 2 shows the results of a 3 hour extracorporeal circulation for hemodialysis with a handmade cellophane membrane (blood flows 200 ml/min). The cellophane membrane is considered to be more blood incompatible than synthetic membranes used for apheresis.

When the bioincompatible apheresis filter is used for apheresis, there is a sudden blood pressure drop and sudden reduction of circulating leukocytes occurred within the frame work of initial 30 min of extracorporeal circulation (FIG. 2). The same situation occurred when unpurified heparin was injected 100 units/kg. The differences of drug induced hypotension and the bioincompatible apheresis column induced hypotension are the former cannot reverse such side effects after injection but the latter can stop these side effects by reducing blood flows for extracorporeal circulation.

Figure 3:
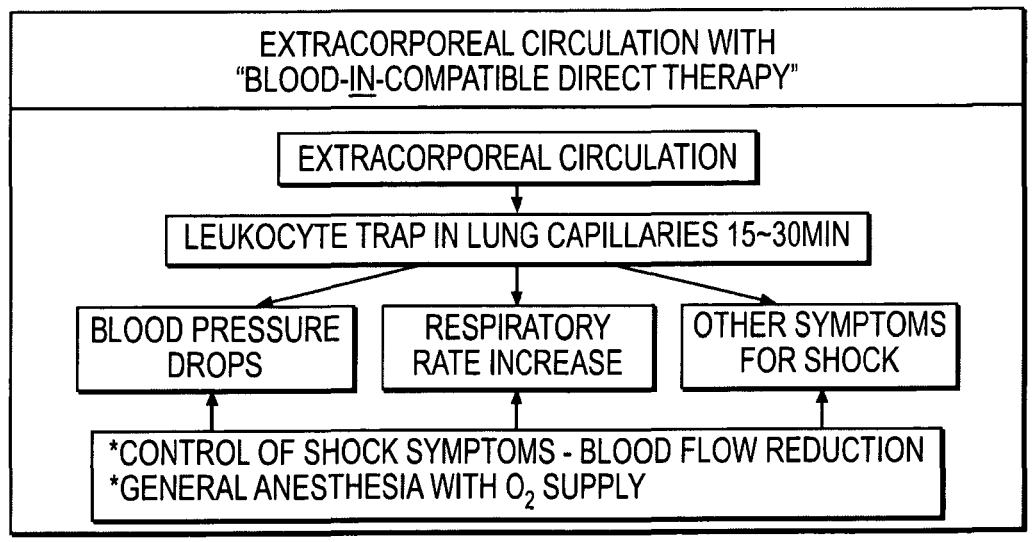
FIG. 3 provides a schematic of the physiological impacts introduced by apheresis using the immunoactivation filter of the invention including transient leukocyte trapping in lung capillaries.

These physiological impacts introduced by the immunoactivating blood perfusion filter of the invention are shown in FIG. 3. The primary cause of these physiological impacts comes from leukocyte trapping in the lung capillaries. Mostly granulocytes are trapped transiently inside of the lung capillaries and subsequently induce transient lymphocyte dominant state in the patient. This is one of the most important signs of the immunoactivation of the patient. Thus, transient reduction of the circulating leukocytes together with hypotension help to facilitate the beneficial therapeutic effects of the invention. The leukocytes are trapped in the lung capillaries during the initial 30 minutes of extracorporeal circulation. Regardless of whether extracorporeal circulation is continued or not, after 30 minutes, release of these trapped leukocytes in the lung capillaries will be initiated. The so-called unsafe "side effects" of bioincompatible blood purification are actually physiological responses that lead to the therapeutic effects on malignant tumors.

Figure 4:
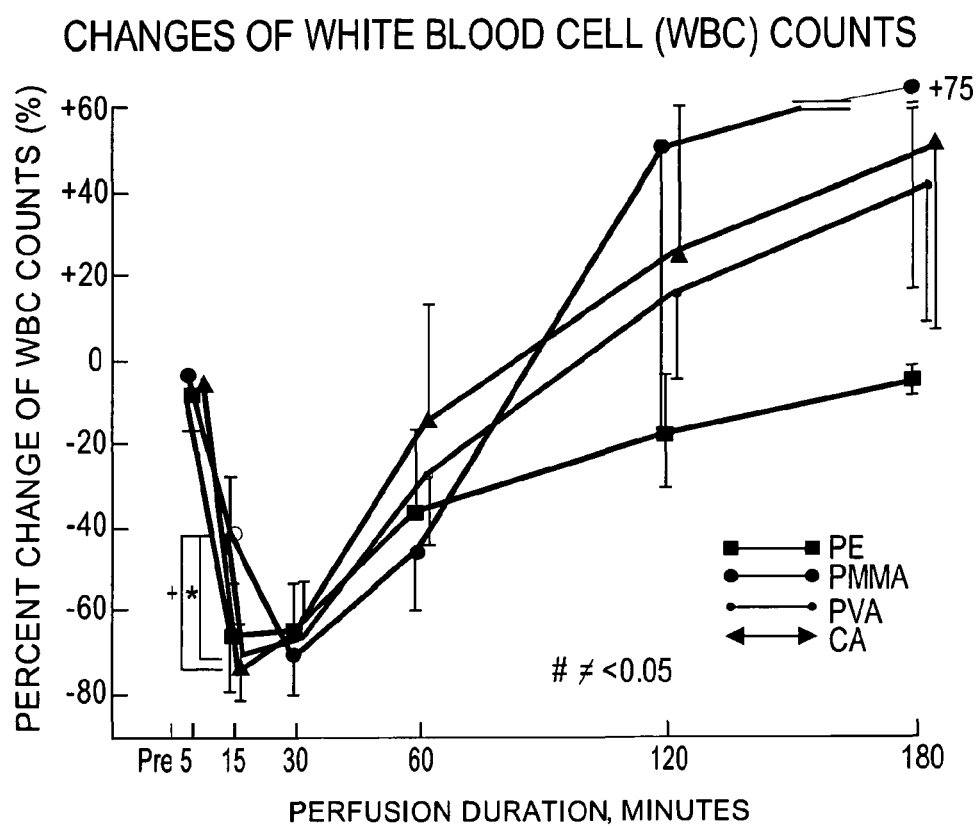
FIG. 4 shows the effect of apheresis on white-blood cell counts in the blood over time using the following bioincompatible materials: polyethylene (PE), polymethylmethacrylate (PMMA), polyvinyl alcohol (PVA), and cellulose acetate (CA).

Transient increases in leukocytes after this 30 minute period of time can occur as shown in FIG. 4. Depending on the different compatibilities of the filter, kinetics of leukocytes returned to circulation are different after these 30 minutes. Leukocyte trapping after extracorporeal circulation during the first 30 minutes is the same with different filters of different material, however, the rate of leukocyte return to the blood circulation are different due to the differing bioincompatibility of the materials.

In addition, monitoring and prevention of side effects are very difficult when using traditional drug therapy and radiation therapies for malignant tumors. During these therapies, patients suffer a great deal of complications, not only losing their hair, but also having many negative physiologies. Yet their therapeutic effects are not certain, and can be expensive. Contrary to traditional therapies for malignant tumors, the direct blood therapy by immunoactivation demonstrates its effects easily in a controllable and monitorable way (Table 3). In others words, it is safer and easier to put patients under proper control of doctors during and after the immunoactivation blood perfusion procedure of the invention using general anesthesia with intratracheal cannulation for 6 hours. Indeed, in the study described in Example 2, all the dogs that were subjected to this immunoactive apheresis therapy were alive and healthy for at least 6-12 months after treatment. This extracorporeal therapy giving the patient a controlled immunological shock, can be performed under general anesthesia with proper blood pressure monitoring, so the patient doesn't have any negative feeling or pain during or after the procedure.

TABLE 3

|  | By Drugs | By Blood Therapy |
|---|---|---|
| Effects | indirect | direct |
| Control of effects | difficult | easy |
| Control of side effects | difficult | easy |
| Monitoring of effects or side effects | difficult | easy |
| Reversal or suppression of effects | difficult | easy |

Method

Injection of bioincompatible material directly into a person is dangerous because it is difficult to remove after immunoactivation takes place. The safe immunoactivation of the patient's immune system can instead be accomplished via extracorporeal apheresis. As described above, there were no immunoactive apheresis filters without introducing so called immunological shock syndrome to patients. Unfortunately, at this time there was no method to control this immunological shock syndrome properly and safely. However, in order to provide proper and clinically effective immunoactivation to cancer patients, it is important to induce controlled immunological shock to patients.

In order to provide a safe apheresis procedure, the method of the invention involves performing the apheresis procedure under general anesthesia. In another embodiment, the apheresis is performed with intratracheal intubation. In another embodiment, proper blood pressure and proper blood gas levels are maintained throughout the procedure. Proper blood gas levels can be maintained using, for example, oxygen supplies administered via the nose, mouth, or trachea. In some embodiments, oxygen is administered through a mask covering the patient's nose and mouth. In another embodiment, oxygen is administered via an intratracheal tube.

For example, when a subject is subjected to an apheresis procedure with a bioincompatible blood perfusion filter according to the invention, sudden hypotension and leukopenia can occur during the initial 15 to 30 minutes of extracorporeal circulation. Blood pressure can decrease by more than 50%. This effect can be reversed after 30 minutes by reducing the rate of blood flow and in general returned to the pre-procedural levels within the framework of one hour. In the instant invention, as discussed below, because of the nature of the immunoactivation that occurs during and after apheresis, the subject is kept on general anesthesia for approximately 6 hours.

In one embodiment of the invention, extracorporeal circulation through an apheresis column according to the invention for one hour with general anesthesia and maintenance of the anesthesia for an additional five hours can provide safe immunoactivation to patients. The initial rate of blood flow through the apheresis column can be about 100 to 200 ml/min, allowing the treatment of one blood volume in about sixty minutes. An extracorporeal circulation rate of approximately 100 ml/min can be achieved by veno-venous needle access. In another embodiment, approximately 100 ml/min blood flows can be maintained during apheresis; If however, at the beginning of the extracorporeal circulation, blood pressure drops to an unsafe level, for example less than 50 mm Hg, then this drop in blood pressure should be rectified. In one embodiment, the blood flow rate can be reduced by 25%. If hypotension continues, then the blood flow rate can be further reduced by 50% of the initial blood flow rate. Also, the oxygen content of the arterial blood can drop together with leukocyte counts, for example less than 20% of the total cell count, during this time. Immediate reduction of the blood flow rate by 25% to 50% can also remedy hypoxia and leukopenia. In one embodiment, the blood flow rate can be reduced from about 100 ml/min to about 75 ml/min or about 50 ml/min.

In another embodiment, the immunoactivation of cellular and molecular factors in the blood is completed in six hours (acute phase). During this period of time, the patient's cardiopulmonary function can be maintained under general anesthesia. Thus, patients do not feel any uncomfortable side effects of induced immunological shock, including dizziness, respiratory difficulties, nausea, vomiting, excessive sweating, fever, chills and shiver.

In one embodiment, the invention provides a method of treating a disease in a patient comprising:
(a) providing an apheresis column including a blood perfusion filter comprising at least one bioincompatible material;
(b) connecting the patient's blood circulation with the apheresis system such that the patient's blood passes through the blood perfusion filter before reentering the patient's body;
(c) placing the patient under general anesthesia and providing physiological support to the patient;
(d) circulating the patient's blood through the apheresis system for about one hour; and
(e) keeping the patient under general anesthesia for at least 5 hours after circulating the patient's blood through the apheresis system,
wherein circulating the patient's blood through the blood perfusion filter activates the patient's immune system thereby treating the disease.

In one embodiment, the invention provides a method of treating a disease in a patient comprising:
(a) providing an apheresis column including a blood perfusion filter comprising at least one bioincompatible material
(b) providing general anesthesia with continuous arterial pressure monitoring and oxygen monitoring of arterial blood via endotracheal intubation;
(c) administering an anticoagulant to the patient;
(d) circulating the patient's blood through the apheresis column for about one hour via veno-venous perfusion; wherein the rate of blood flow through the apheresis column is about 100 to 200 mL/min;
(e) monitoring the patient's blood pressure and blood oxygen levels;
(f) keeping the patient under general anesthesia for at least 5 hours after circulating the patient's blood through the apheresis system while monitoring the patient for signs of immunoactivation and cardiopulmonary stability; and
(g) removing the patient from general anesthesia after confirming the recovery of lung functions to pre-apheresis levels.

In another embodiment, the invention provides for the use of:
(a) an apheresis system including a blood perfusion filter comprising at least one bioincompatible material, wherein the apheresis system is connected to a patient's blood circulation such that the patient's blood can pass through the blood perfusion filter before reentering the patient's body; and
(b) a general anesthetic for anesthetizing the patient during use of the apheresis system and for at least 5 hours following that use
for treating a disease in a patient, wherein use of the apheresis system activates the patient's immune system thereby treating the disease.

Figure 26:
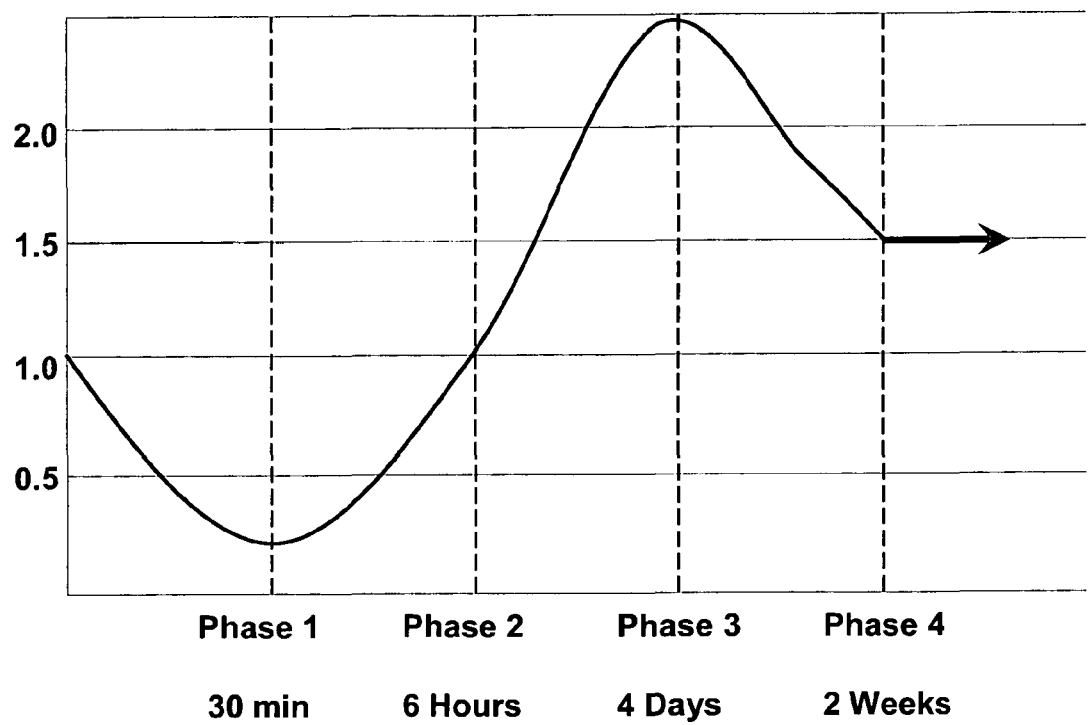
FIG. 26 shows a graphic of leukocyte kinetics in the blood of an apheresis recipient after treatment by the method of the invention. The X axis shows each phase in relevance to the amount of time that has passed since apheresis began. The Y axis shows the relevant units of leukocyte counts, with 1.0 constituting the level of leukocytes in the blood at the start of apheresis.

The method of the invention results in significant changes in leukocyte population in the patient's blood and in a transient increase of some of cytokines. As shown in FIG. 26, four different phases of leukocyte kinetics spanning two weeks, emerged as a result of the method. In phase 1, which is less than 30 minutes after extracorporeal circulation is initiated, transient reduction of the leukocytes inside of the blood occurs primarily by trapping them inside of the lung capillaries. With the use of bioincompatible materials in the apheresis column, more reduction of granulocytes (near 100%) compared with lymphocytes (about 40%) can occur, creating a lymphocyte dominant state in the blood. After 30 minutes, granulocytes are gradually released from the lung. In general, one hour extracorporeal-circulation can generate sufficient immunoactivation effects.

In phase 2, leukocytes are released from lung capillaries and leukocyte counts become normalized in approximately 6 hours. During these 6 hours, most granulocytes are released from the lung. This is also the lymphocyte dominant stage in which a massive transient increase in cytokines occurs, which in turn leads to the death of tumor cells in the patient's body. During these 6 hours, lung function may require assistance. The general anesthesia with ample supply of oxygen by intratracheal intubation can treat hypoxia during this period of time.

In phase 3, four days after apheresis, lymphocyte counts increase substantially higher in spite of marked reduction of granulocytes during the initial six hours. Leukocytes, including granulocytes and lymphocytes, can also increase also more than two fold over pre-apheresis levels. An even more substantial increase in monocyte population, as compared to granulocytes and lymphocytes, also occurs during this phase. During this period of time, these increased monocytes and granulocytes should be able to eliminate the dead tumor cells. Meanwhile, lymphocytes are still present at high levels.

In phase 4, all of these abnormally increased leukocyte counts return to the pre-apheresis levels after two weeks. In one embodiment, if unexpectedly higher levels of immunoactivation and subsequent excessive destruction of tumor cells occurs after two weeks, apheresis procedures to remove these cellular debris and immunoactive agents can be applied to maintain patient's safety.

In one embodiment, apheresis can be administered to the patient according to the invention once. In another embodiment, apheresis can be administered to the patient more than once. In this case, each apheresis treatment occurs every two weeks. In yet another embodiment, treatment is provided to the patient at least three times, with each treatment occurring every two weeks. In this embodiment, overall treatment of the patient would be completed in six weeks. In another embodiment, apheresis treatment according to the invention may be supplemented by conventional anticancer therapies to augment the invention's effects of immunostimulation.

It is not required that the patient's blood travel directly from the apheresis column back into the patient's body. In one embodiment, the patient's blood can flow into the apheresis column of the invention and then be collected for later administration to the patient. Thus, it is possible to establish immunoactivation by exposing the harvested blood from the patient to the filter with bioincompatible material column and reinjection to the patient.

The main technical features of extracorporeal apheresis according to the invention include (1) achievement of extracorporeal circulation through a bioincompatible blood perfusion filter in about 60 minutes; (2) phase 2 immunoactivation can be completed in six hours during which cellular and cytokine activation occurs; and (3) physiological responses to treatment occur in about 30 minutes and include hypotension, leukopenia, and respiratory difficulties such as hypoxia. These physiological responses are safely and unpainfully accepted by the patient who is under general anesthesia.

Aheresis Column Assemblies Useable in the Methods of the Invention

Figure 5A:
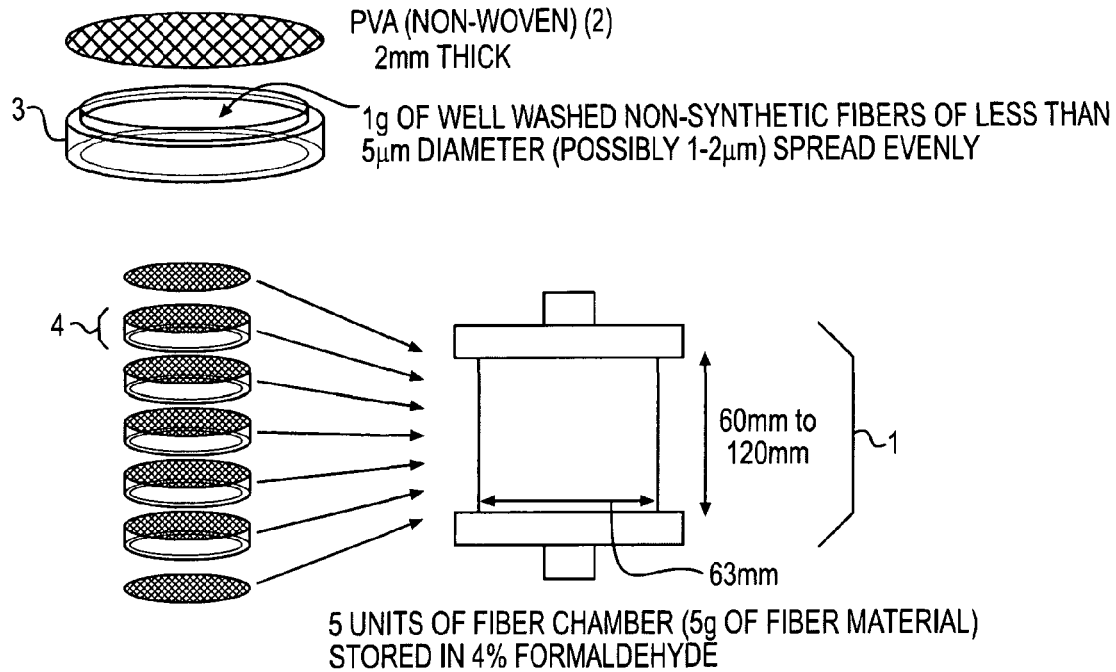
FIG. 5A provides a schematic of one example of an apheresis column according to the invention.

FIG. 5A provides one embodiment of an acrylic apheresis column that can be used in the method of the invention. A small acrylic chamber (3) holds approximately 1 g of washed fibers of about 5 µm or less. These fibers are supported in the small chamber by a non-woven mesh of PVA (2) which is about 2 mm thick. The non woven PVA mesh (VW100) was provided Kuraray Inc, Tokyo Japan. Each small chamber including the prepared fibers and the PVA mesh constitutes a filtering unit (4). Five to 10 filtering units can be stacked into the apheresis column (1). In one embodiment, 5 filtering units are used in which case the column's height is about 60 mm. In another embodiment, 10 filtering units are used in which case the column's height is about 120 mm.

In one embodiment, the filtering units may be packed inside the chamber in such a way as to allow approximately 400 ml of priming volume, the volume of priming solution that is run through the column before introduction of blood, in the chamber. The packing density of the filters can be up to approximately 10% (grams/volume).

Bioincompatible Materials

Trapping leukocytes in the lung capillaries helps to establish the lymphocyte dominant state during which immunoactivation occurs. In the case of cancer, it is during this time that cancer cells can be destroyed. Optimal bioincompatible material will remove granulocytes from the blood by trapping them inside the apheresis column and, for leukocytes that reenter the body, exposure to the bioincompatible material can cause those leukocytes to become temporarily trapped in the lungs. Using fibers with a small diameter helps to facilitate these effects. In one embodiment, the fibers have a diameter of 5 µm or less. In another embodiment, the fibers have a diameter of 1-2 5 µm.

Natural fibers that are useable with the apheresis column of the invention include, but are not limited to cotton and silk.

Smaller diameter cotton fibers from Egypt can facilitate leukocyte trapping in the lungs. Contrary to the synthetic polymers, natural cotton fibers are composed by multiple molecular complexes and are more bioincompatible. Among all cotton fibers, Egyptian cotton fibers have smaller diameters than Pakistani cotton and Australian cotton fibers. Thus bioincompatible filters that are made from Egyptian cottons are expected to produce the most effective immunoactive filters from the group of plant fibers. Each type of cotton is harvested in its country of origin and can be obtained from Marubeni America Corporation, Houston, Tex.

Among natural zoological fibers, silk fibers are the smallest in diameter. Among all silks, the smallest fiber sizes were demonstrated by "Kanton" silk and "Japanese" silk. Japanese silk is produced by Japanese manufacturers while Kanton silk is manufactured in China. Both types of silk can be obtained from Marubeni America Corporation, Houston, Tex. The smallest diameters of the silk fibers are almost analogous to the fiber diameters of Egyptian cotton. They were less than 5 µm, typically 1-2 µm. However, zoological fibers are more complex structures with multiple different bioincompatible components (particularly protein groups) over above the plant fibers. Thus they are more bioincompatible over above the synthetic fibers or the natural plant fibers.

Foreign proteins from the silk worms can act as immunostimulators, allowing the silk to yield better stimulation of the patient's immune system. Thus, optimal immunoactivation filter can be obtained by using the silk. It is expected that an immunoactivation column made with silk fibers should be able to treat malignant tumors by extracorporeal blood perfusion.

In some embodiments, the natural fibers of the invention may be biolized. As used herein, the term "biolized" refers to a crosslinking procedure that links homogenous proteins present in the fiber to produce a smooth, consistent surface on the fiber. Fibers may be biolized chemically or via irradiation techniques. Fibers may be biolized chemically by using chemical agents including, but not limited to, formaldehyde and glutaraldehyde. In one embodiment, fibers are soaked in 10% formaldehyde for at least 48 hours. In another embodiment, fibers can be stored in a 0.45% solution of glutaraldehyde longer than 2 weeks and as long as 5 years. If the bioincompatible material inside the apheresis column has been biolized, the column should be washed with normal saline to remove residual aldehyde prior to clinical usage.

EXAMPLES

Example 1

Change in Blood Cell Counts Upon Contact with Bioincompatible Materials

Figure 7:
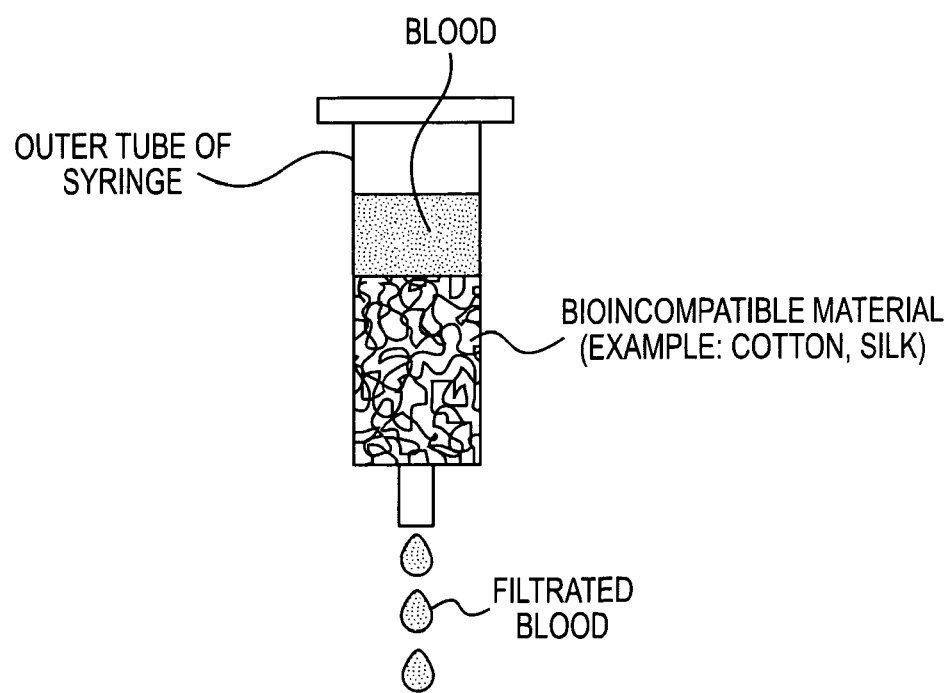
FIG. 7 provides a schematic of a miniature blood filtering column including a syringe and a bioincompatible material.
Figure 8A:
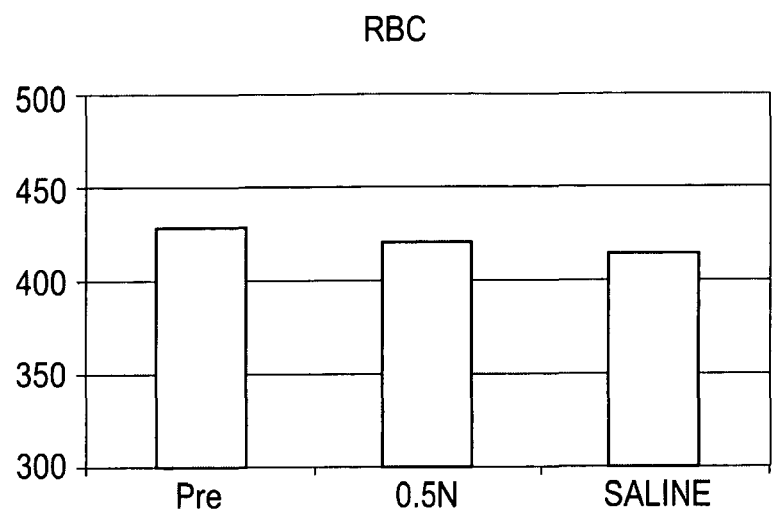
FIG. 8 shows the effects of treating Egyptian cotton with acid and alkali or with saline on counts of certain cell types in blood after filtration through the treated cotton: (A) red blood cells (RBCs), (B) white blood cells (WBCs), (C) platelets (Plt), and (D) neutrophils and lymphocytes. "Pre" samples indicate cell counts taken from blood samples prior to filtration. For RBCs, the Y axis measures number of cells×$10^4$ per microliter of filtered blood. For WBCs, the Y axis measures number of cells per microliter of filtered blood. For Plt, the Y axis measures number of cells×$10^4$ per microliter of filtered blood. For neutrophils and lymphocytes, the Y axis measures number of cells per microliter of filtered blood.
Figure 8B:
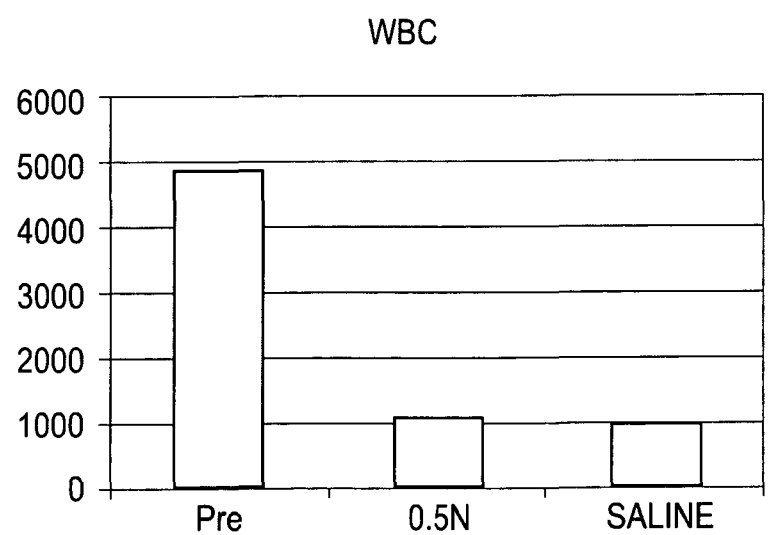
Figure 8C:
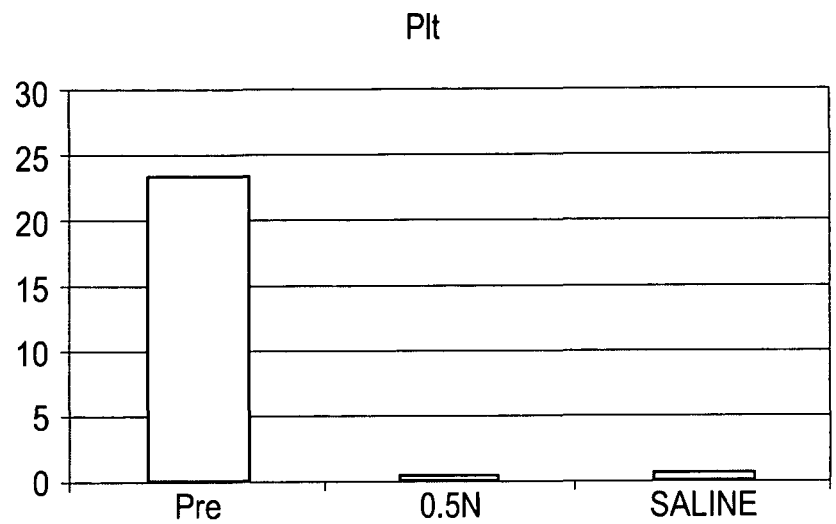
Figure 8D:
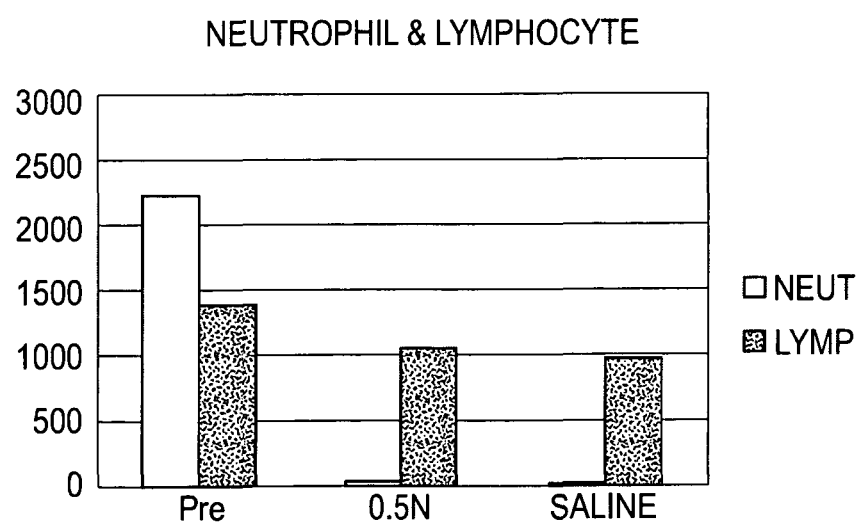
Figure 9A:
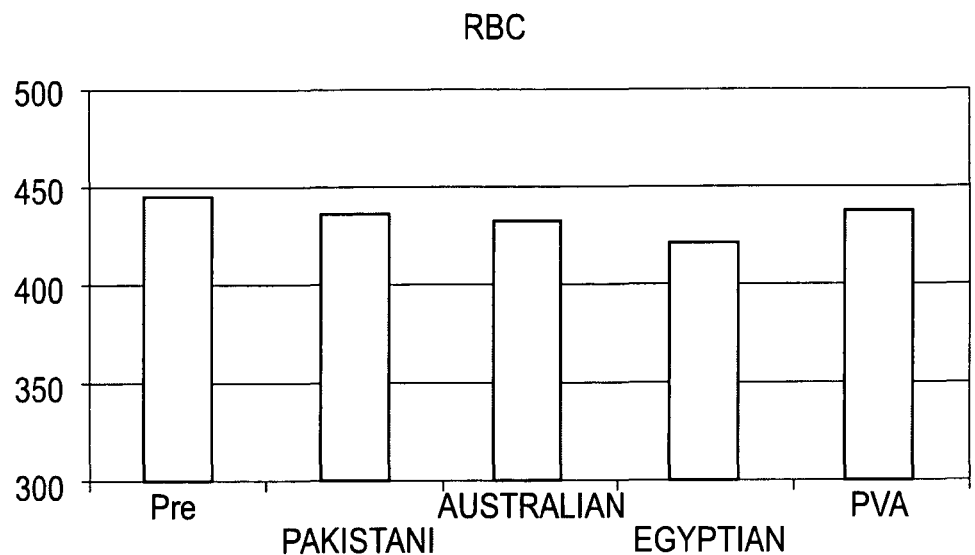
FIG. 9 shows a comparison between the ability of different types of cotton fibers and PVA fibers to remove certain cell types from whole blood: (A) RBCs, (B) WBCs, (C) Plt, and (D) neutrophils and lymphocytes. "Pre" samples indicate cell counts taken from blood samples prior to filtration. For RBCs, the Y axis measures number of cells×$10^4$ per microliter of filtered blood. For WBCs, the Y axis measures number of cells per microliter of filtered blood. For Pit, the Y axis measures number of cells×$10^4$ per microliter of filtered blood. For neutrophils and lymphocytes, the Y axis measures number of cells per microliter of filtered blood.
Figure 9B:
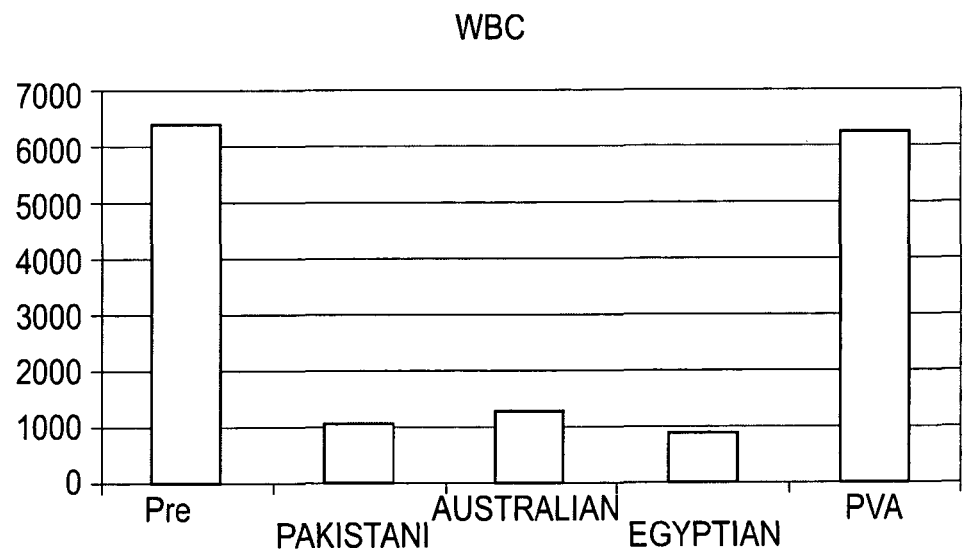
Figure 9C:
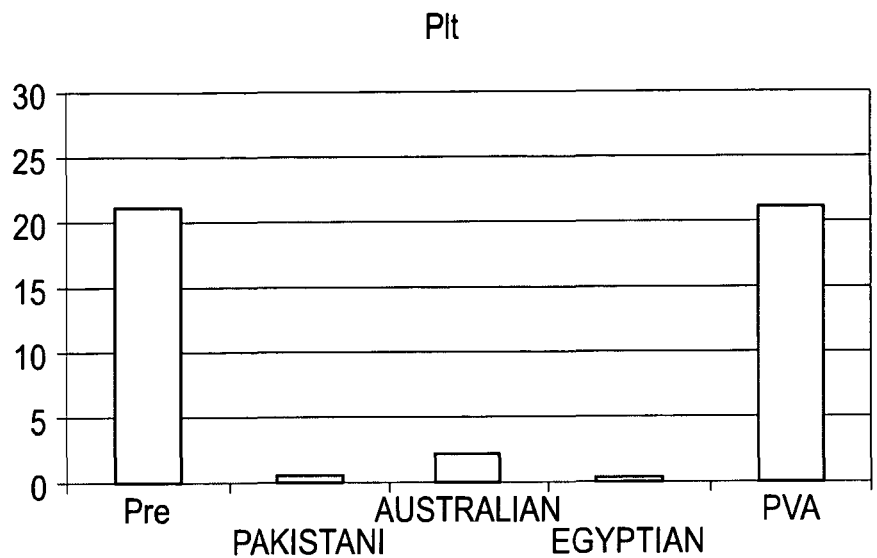
Figure 9D:
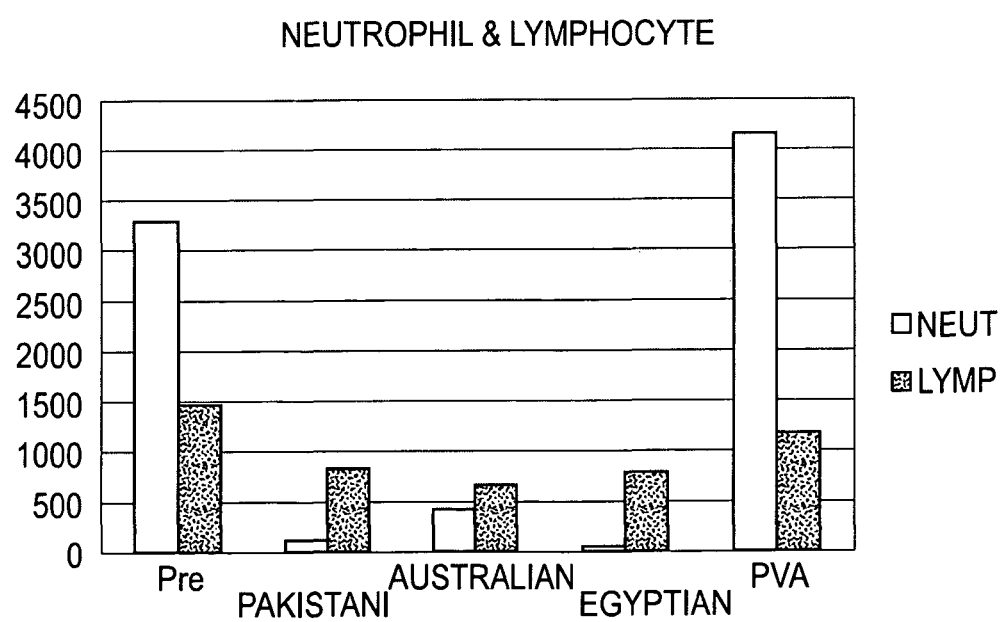

Types of cotton and silk were tested under varying conditions for their ability to filter out different cell types from human whole blood. For these in vitro experiments, a 5 ml syringe was packed a bioincompatible material to a 4 ml volume inside the syringe, resulting in a density of 0.125 g/ml. See FIG. 7. Whole blood was obtained from a normal, healthy human and 1 unit of heparin sodium was added per milliter of blood to reduce clotting. Blood preparations were used in the experiments within 30 minutes of collection. During filtration at 22° C., the treated blood was poured into the top of the syringe, filtered through the bioincompatible material, and then collected from the bottom of the syringe. The resulting filtered blood was then analyzed for the presence of different cell types.

The granulocyte removal rate of Egyptian cotton treated with a 0.5 N acid solution and a 0.5 N alkali solution was compared to the removal rate obtained with Egyptian cotton treated with saline (Baxter Corp. catalog no. 281324). The raw Egyptian cotton was obtained from Marubeni America Corporation and was prepared by successive soaking with 0.5N NaOH (S320-500 Fisher Scientific), water, 0.5N HCl (SA48-500, Fisher Scientific), water, and normal saline for about 30 minutes in each solution. Egyptian cotton was also soaked in normal saline alone. After treatment of the cotton, 0.5 g of the acid/alkaline treated or the saline treated cotton was put into the syringe in a 4 ml volume, resulting in a fiber density of 0.125 g/ml. Eight milliliters of blood were poured into the syringe miniature column. The first 4 ml of filtered blood was discarded to prevent dilution by normal saline. The remaining 4 mls of filtered blood was collected and compared to pre-filtered blood for WBC and RBC counts.

As shown in FIG. 8, there were no differences between the removal rate of the acid/alkali treated Egyptian cotton and the saline treated cotton. Both treatments resulted in comparable removal of red blood cells (RBCs), white blood cells (WBCs), and platelets. More specifically, neutrophils and lymphocytes were also removed at comparable rates between the two cotton treatment groups. The number of lymphocytes reduced slightly in comparison to the number of lymphocytes in prefiltered blood (FIG. 8D). These results demonstrate that Egyptian cotton maintained its ability to remove granulocytes, as measured by the reduction in neutrophil count, in the presence of chemical treatments that may be used in preparation of the cotton (i.e., to remove grease, sterilize, and/or neutralize the cotton).

Four types of cotton, and PVA fibers as a negative control, were tested for the most effective removal rate of granulocytes as measured by the removal of neutrophils from filtered blood. The four types of cotton tested were Pakistani cotton (Marubeni America Corporation), Australian cotton (Marubeni America Corporation), and Egyptian cotton. Both cotton and PVA were rinsed in normal saline before 0.5 g of each type of cotton and PVA was put into the 5 ml syringe in a volume of 4 mls, resulting in a fiber density of 0.125 g/ml. Eight milliliters of whole blood were filtered through the syringes and the second 4 mls were collected for analysis.

Figure 10:
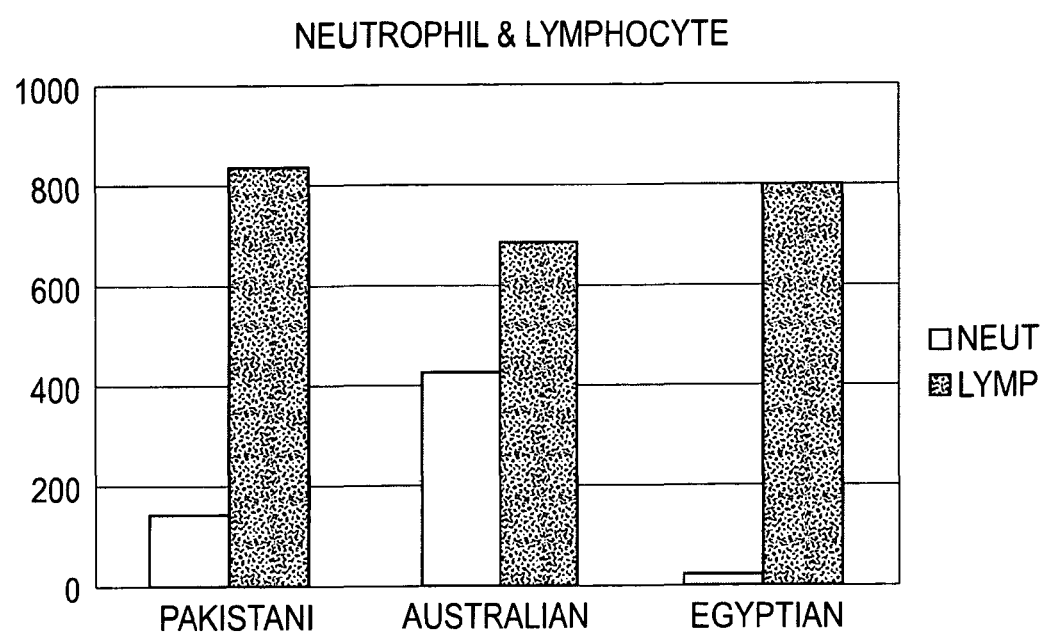
FIG. 10 shows a comparison between the ability of different types of cotton fibers to remove neutrophils and lymphocytes from whole blood.

As shown in FIG. 9, almost 100% granulocyte removal was demonstrated by each of the cottons tested in comparison to the PVA negative control, with Egyptian cotton providing the best result. See FIG. 9D. See also FIG. 10. In addition, RBCs were not filtered out by any of the cotton types while the majority of platelets were removed. See FIGS. 9A and 9C. Regarding lymphocytes, each type of cotton exhibited slightly different levels of lymphocyte removal, with Australian cotton removing the most lymphocytes.

Figure 11A:
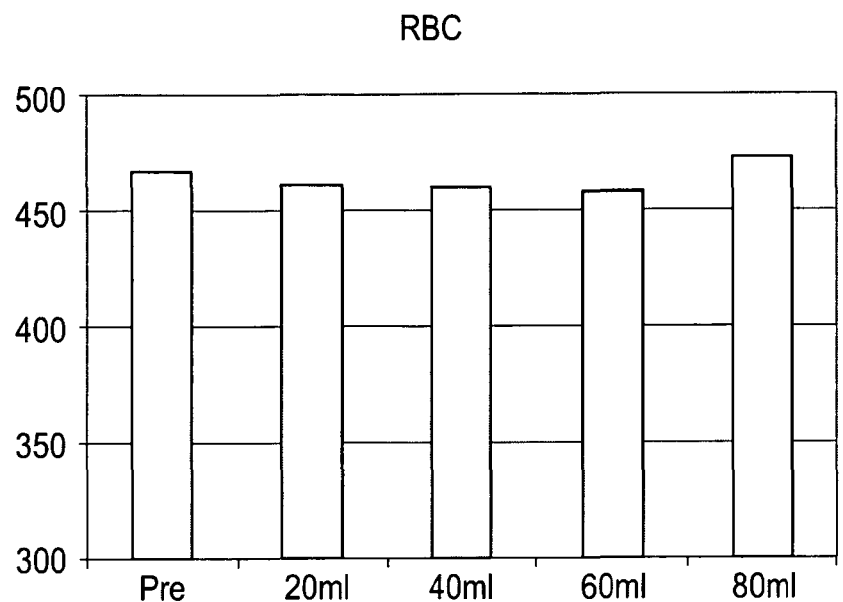
FIG. 11 shows the ability of Egyptian cotton fibers, when at a density of 0.125 g/ml, to remove certain cell types from various volumes of whole blood: (A) RBCs, (B) WBCs, (C) Pit, and (D) neutrophils and lymphocytes. "Pre" samples indicate cell counts taken from blood samples prior to filtration. The Y axis of each figure measures the number of cells per microliter of filtered blood. RBCs and Plt were measured as the number of cells×$10^4$/μl. WBCs and neutrophils/lymphocytes were measured as the number of cells/μl.
Figure 11B:
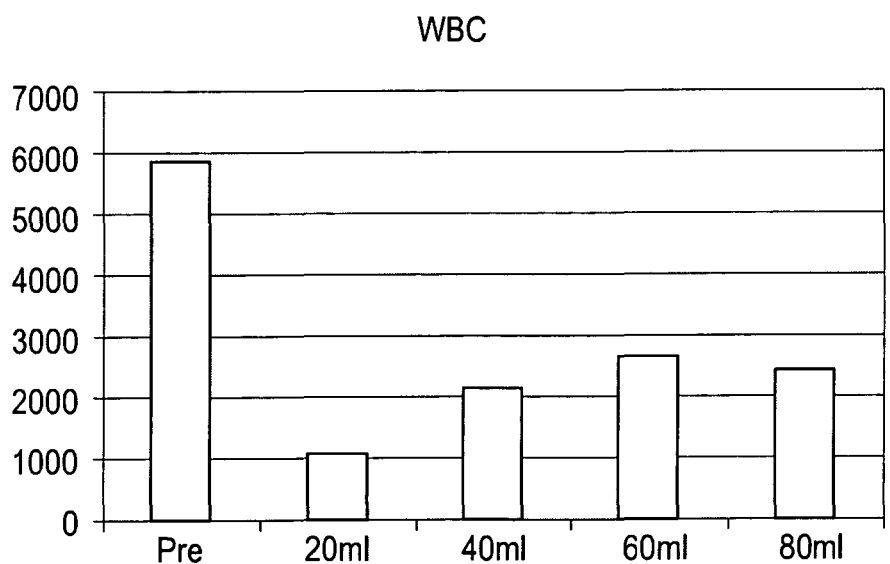
Figure 11C:
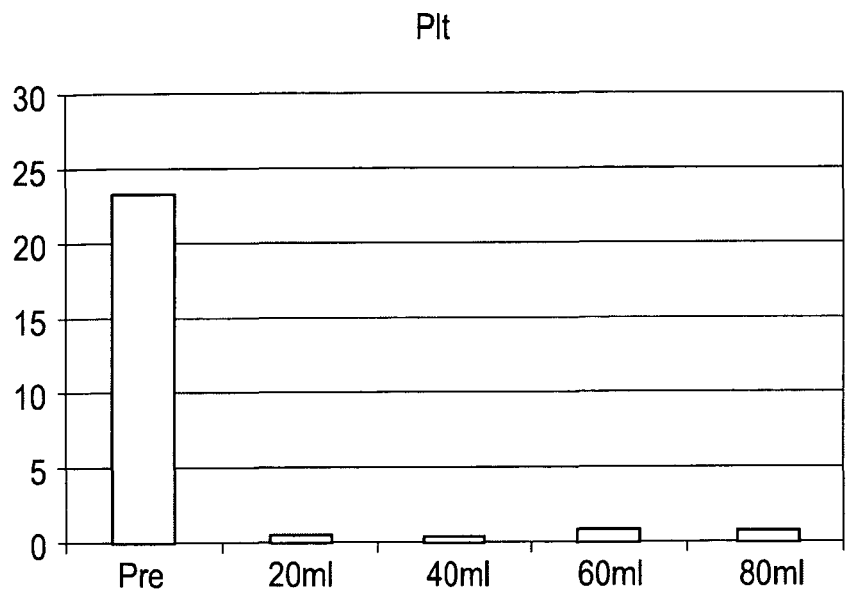
Figure 11D:
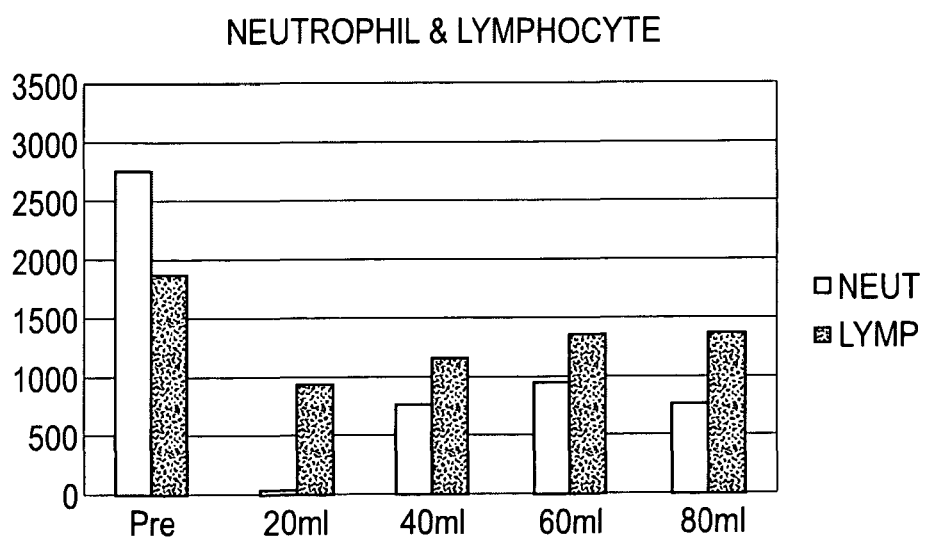
Figure 12A:
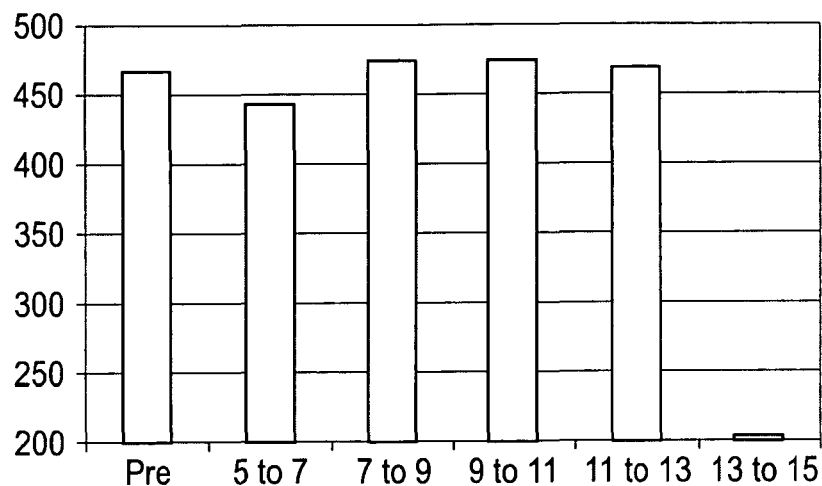
FIG. 12 shows the ability of Egyptian cotton fibers, when at a density of 0.05 g/ml, to remove certain cell types from various volumes of whole blood: (A) RBCs, (B) WBCs, (C) Plt, and (D) neutrophils and lymphocytes. "Pre" samples indicate cell counts taken from blood samples prior to filtration. The Y axis of each figure measures the number of cells per microliter of filtered blood. RBCs and Plt were measured as the number of cells×$10^4$/μl. WBCs and neutrophils/lymphocytes were measured as the number of cells/μl.
Figure 12B:
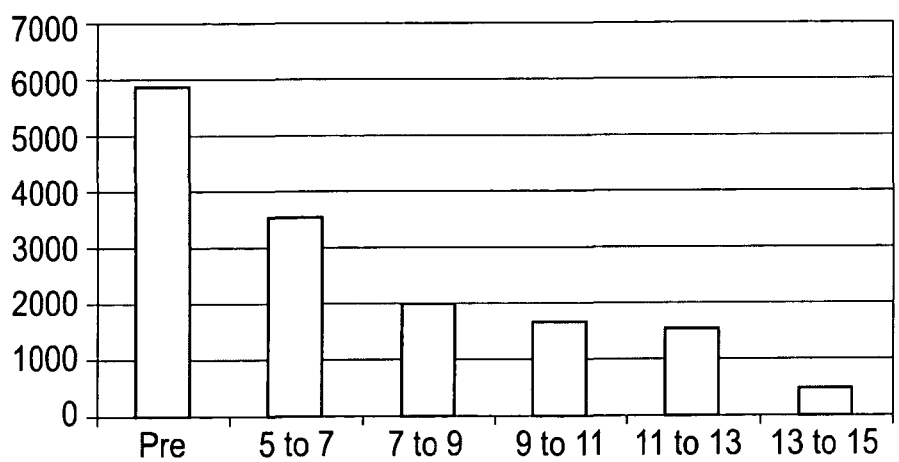
Figure 12C:
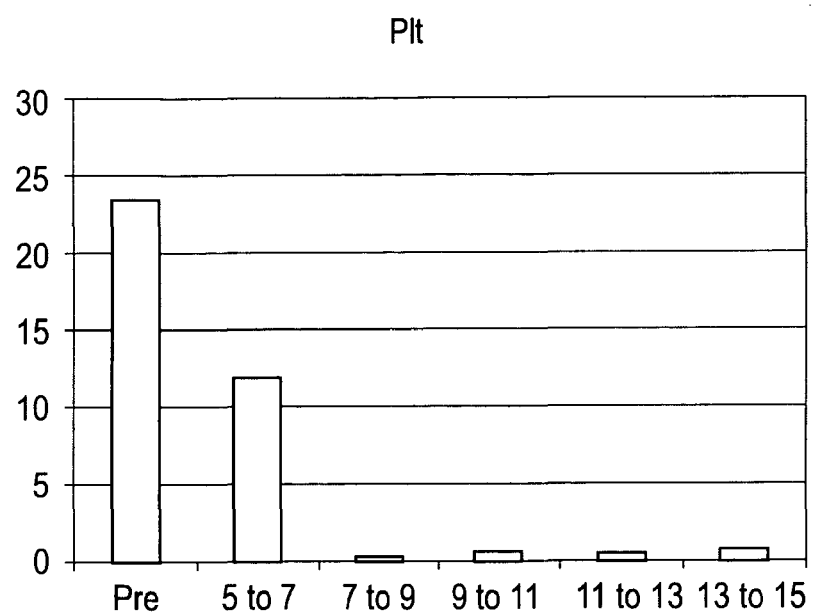
Figure 12D:
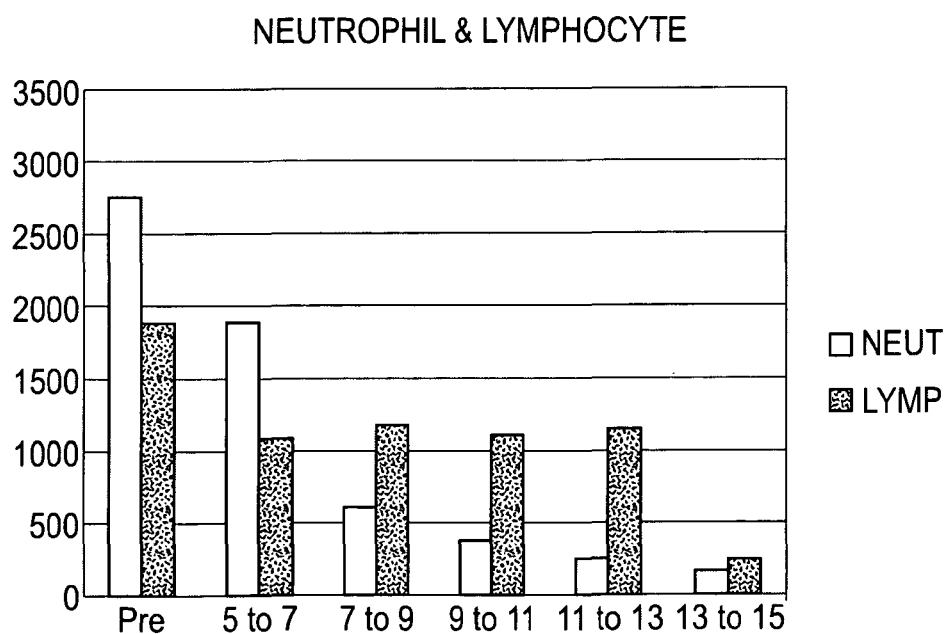
Figure 13A:
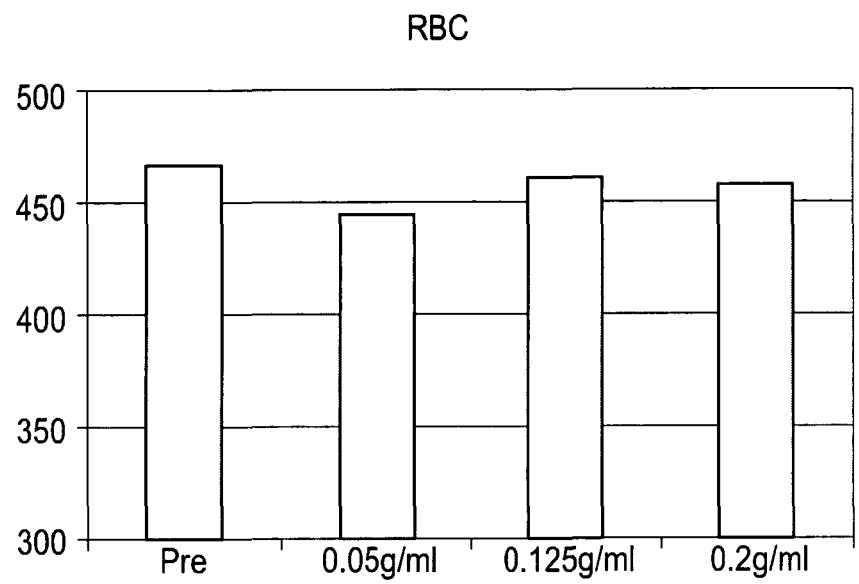
FIG. 13 shows the effect of the density of Egyptian cotton fibers on their ability to remove certain cell types from various volumes of whole blood: (A) RBCs, (B) WBCs, (C) Plt, and (D) neutrophils and lymphocytes. "Pre" samples indicate cell counts taken from blood samples prior to filtration.
Figure 13B:
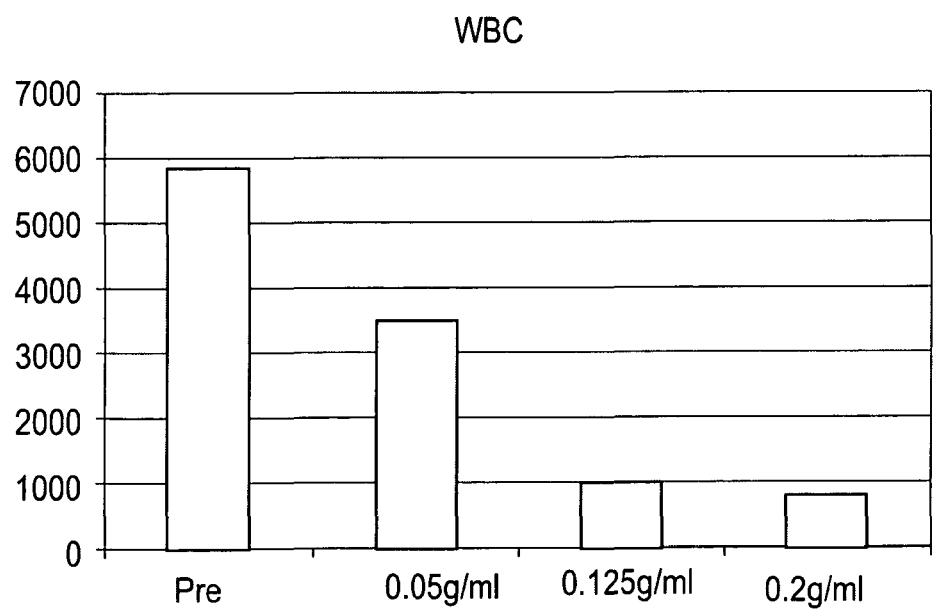
Figure 13C:
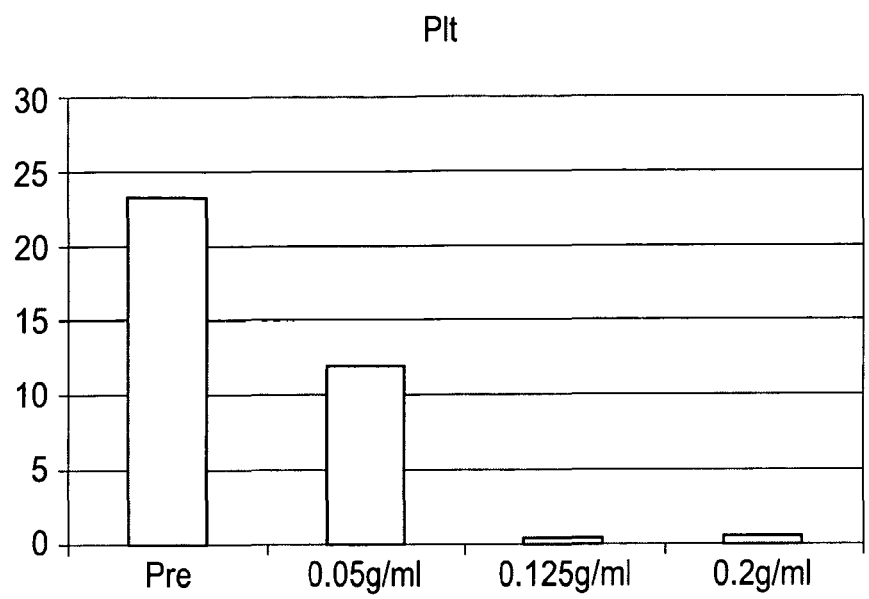
Figure 13D:
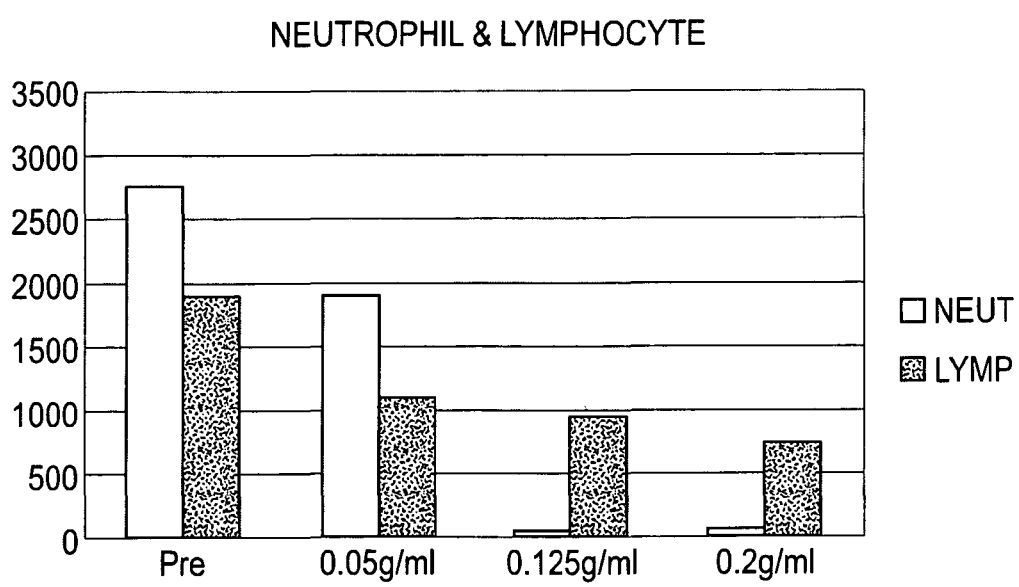

The effect of fiber density on the rate of granulocyte removal was also assessed using Egyptian cotton treated with saline as described above. Egyptian cotton was packed into syringes at densities of 0.125 g/ml and 0.05 g/ml. For the 0.05 g/ml density, 2 grams of Egyptian cotton was packed into a 4 ml syringe. The 0.125 g/ml density columns were prepared as described above. For the 0.125 g/ml density, different blood volumes ranging from 20 ml to 80 ml were filtered through, using a fresh mini column for each blood volume that was tested. For the 0.05 g/ml density, blood volumes ranging from 5 to 15 ml were tested. For each density, the first 4 ml of filtered blood was thrown away to prevent dilution by the normal saline and thereafter, filtrated blood was collected in 2 ml batches. As shown in FIG. 11D, Egyptian cotton, when at a density of 0.125 g/ml, was able to remove some granulocytes, as measured by neurtophil removal, even when 80 ml of whole blood were filtered, although removal was most efficient when 20 mls of whole blood were filtered. The efficiency of granulocyte removal decreased with increasing blood volume. Blood volume did not affect the rate of removal of RBCs or platelets among the blood volumes tested at the 0.125 g/ml density. At 0.125 g/ml density, the Egyptian cotton could keep removing about 70% of the neutrophils up to 80 ml of processed blood volume. FIG. 12D shows that for the 0.05 g/ml density, the efficiency of WBC removal decreased with increasing blood volume. At 11 to 13 ml of filtered blood volume, granulocyte removal was most optimal, while retaining the presence of lymphocytes in the filtered blood. In as little as the first 5 to 7 mls the mini column was able to remove granulocytes, as measured by neutrophil removal.

In FIG. 13, three fiber densities were tested for efficiency of granulocyte removal at a single blood volume Fiber densities of 0.05 g/ml, 0.125 g/ml, and 0.2 g/ml were compared. The 0.05 and 0.125 g/ml density mini columns were prepared as described above. For the 0.2 g/ml density column, 0.2 grams of Egyptian cotton was packed into a 1 ml volume in a 4 ml syringe. When testing the 0.05 g/ml density column, 7 mls of whole heparin-treated blood was filtered through the column. The first 5 mls were discarded and the remaining 2 mls were collected for analysis. For the 0.125 g/ml density, 22 mls of whole heparin-treated blood was filtered through the column. The first 20 mls were discarded and the remaining 2 mls were collected for analysis. For the 0.2 g/ml density column, 5 mls of whole heparin-treated blood was filtered through the column. The first 3 mls of filtered blood were discarded and the remaining 2 mls were collected for analysis. The difference in fiber densities resulted in comparable levels of RBC removal. For WBCs in general, however, a density of 0.05 g/ml did not remove WBCs as well as densities of 0.125 and 0.2 g/ml. Likewise, fiber densities of 0.125 g/ml and 0.2 g/ml worked best to remove granulocytes, as demonstrated by neutrophil counts, while allowing some lymphocytes to pass through the mini column. Thus, a fiber density of at least 0.125 g/ml worked well to remove granulocytes.

Figure 14A:
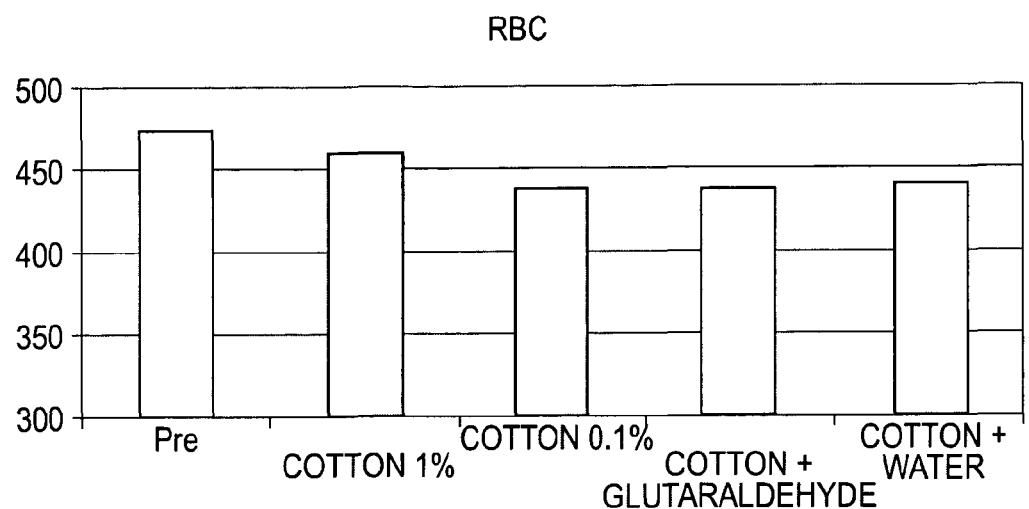
FIG. 14 shows the effect of biolization on the ability of Egyptian cotton fibers to remove (A) RBCs and (B) WBCs from whole blood. Concentrations of 1%, 0.1%, and 0% gelatin were used for biolization. For the 0% sample, only gluteraldehyde was used. Nonbiolyzed samples were treated with water. "Pre" samples indicate cell counts taken from blood samples prior to filtration.
Figure 14B:
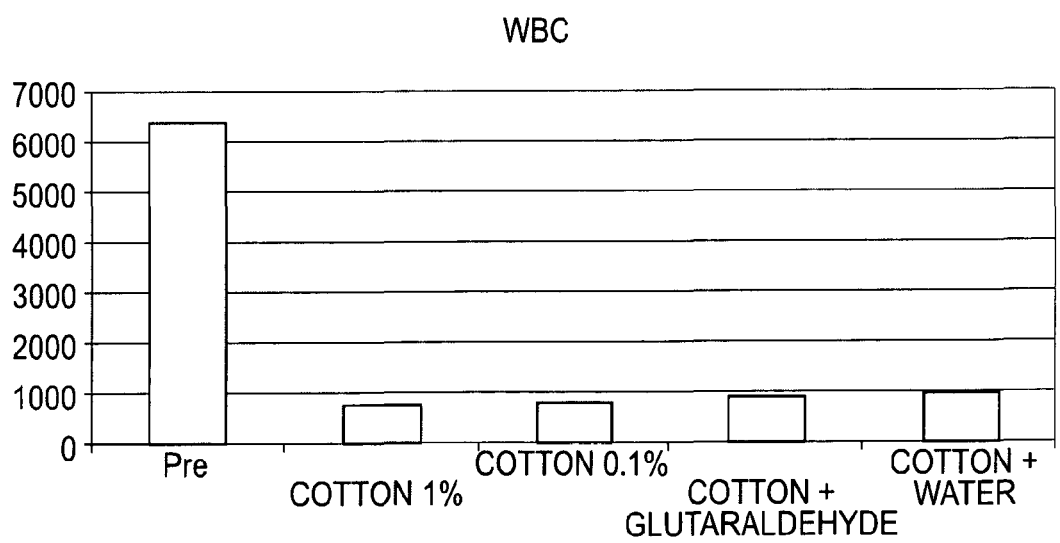
Figure 15A:
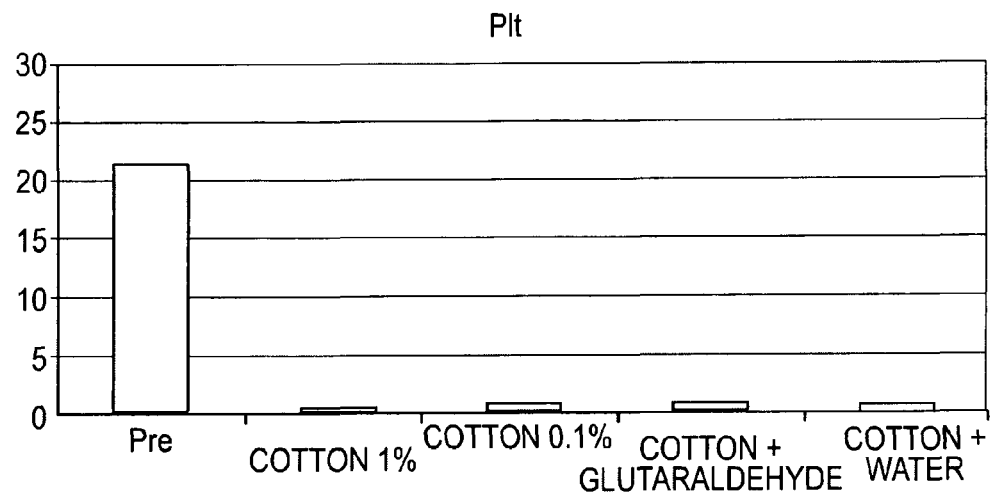
FIG. 15 shows the effect of biolization on the ability of Egyptian cotton fibers to remove (A) Plts and (B) neutrophils and lymphocytes from whole blood. Concentrations of 1%, 0.1%, and 0% gelatin were used for biolization. For the 0% sample, only gluteraldehyde was used. Nonbiolyzed samples were treated with water. "Pre" samples indicate cell counts taken from blood samples prior to filtration.
Figure 15B:
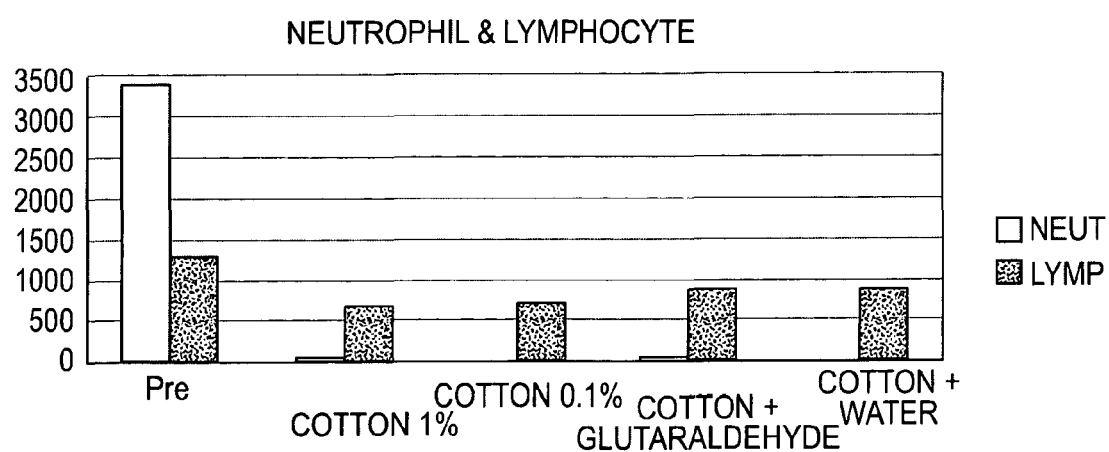
Figure 16A:
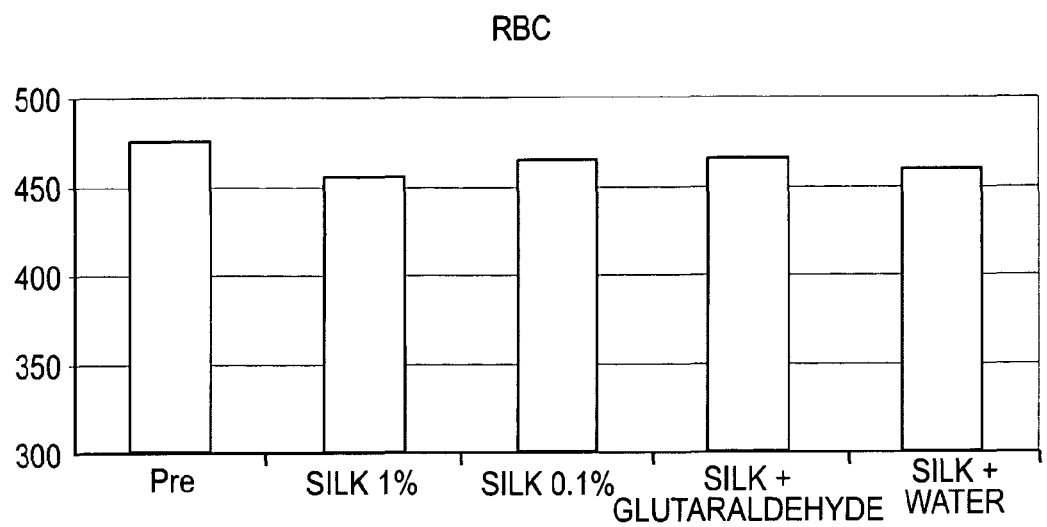
FIG. 16 shows the effect of biolization on the ability of silk fibers to remove (A) RBCs and (B) WBCs from whole blood. Concentrations of 1%, 0.1%, and 0% gelatin were used for biolization. For the 0% sample, only gluteraldehyde was used. Nonbiolyzed samples were treated with saline. "Pre" samples indicate cell counts taken from blood samples prior to filtration.
Figure 16B:
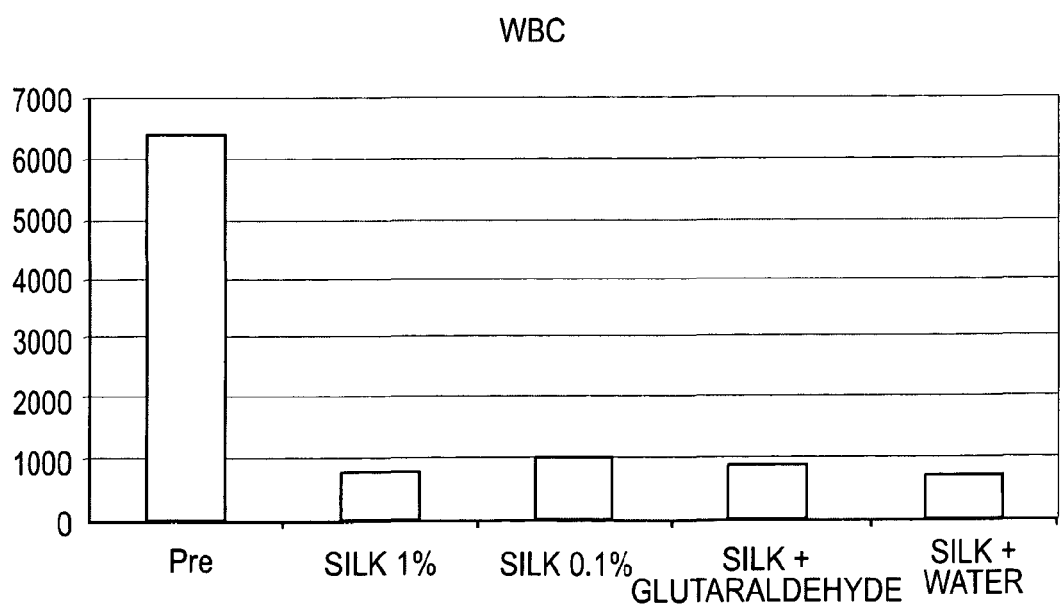
Figure 17A:
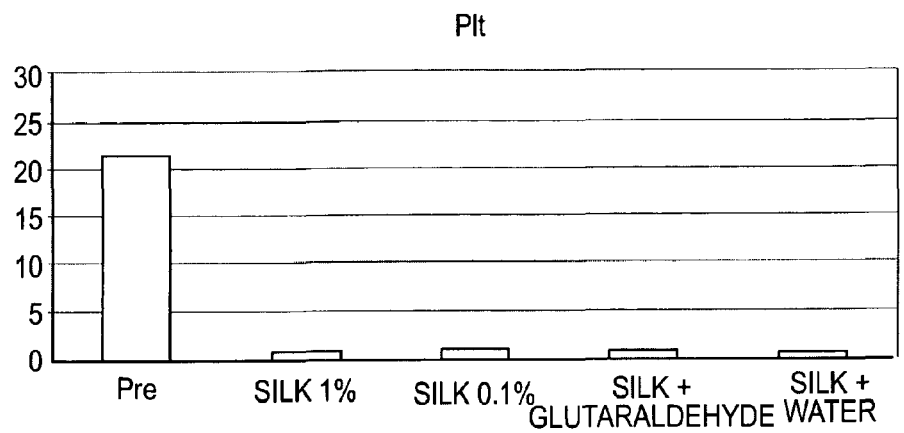
FIG. 17 shows the effect of biolization on the ability of silk fibers to remove (A) Plts and (B) neutrophils and lymphocytes from whole blood. Concentrations of 1%, 0.1%, and 0% gelatin were used for biolization. For the 0% sample, only gluteraldehyde was used. Nonbiolyzed samples were treated with saline. "Pre" samples indicate cell counts taken from blood samples prior to filtration
Figure 17B:
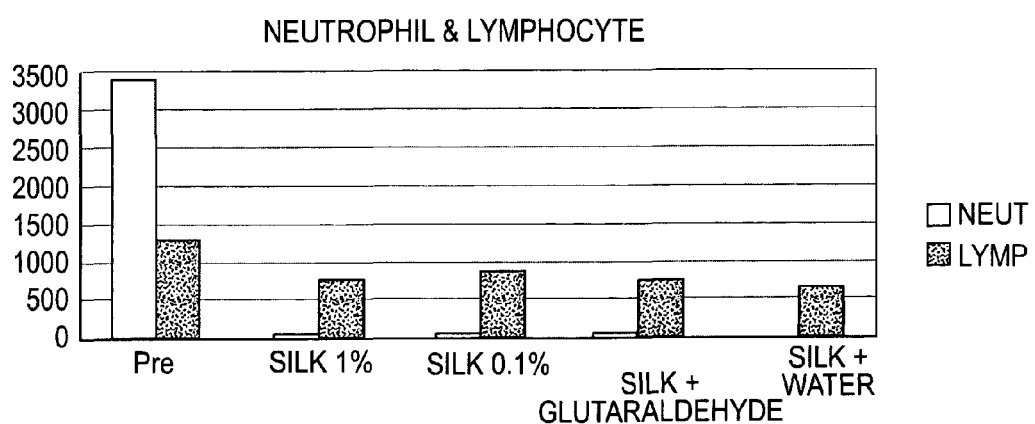

The effect of biolization on Egyptian cotton fibers on the efficiency of granulocyte removal was assessed. Cotton fibers were biolized using three kinds of combination treatments: 0.4% glutaraldehyde crosslinkings followed by coating fibers with 1%, 0.1% or 0% gelatin. In the case of 0% gelatin, fibers were biolized with glutaraldehyde only. For biolization, fibers were soaked in glutaraldehyde for more than 24 hours. The fibers were then coated in a gelatin solution (Fisher Scientific; Cat No. G7-500). Cotton fibers were also soaked in water alone, and acted as a positive control. As shown in FIG. 14, all three treatments resulted in comparable RBC removal among the samples. For WBCs, all three treatments resulted in significant removal of WBCs from the filtered blood. See FIG. 14. FIG. 15 shows that that all three treatments resulted in very good platelet removal and complete granulocyte removal while allowing some lymphocytes to pass through the mini column. A similar study was conducted using silk fibers instead of Egyptian cotton, yielding similar results. See FIGS. 16 and 17.

Figure 18A:
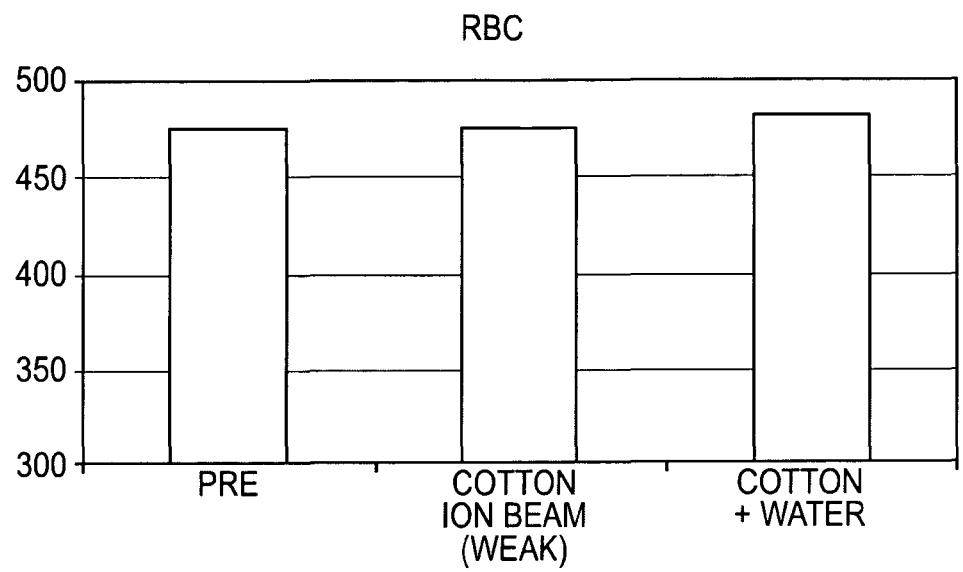
FIG. 18 shows the effect of biolization with weak ion-beam irradiation on the ability of Egyptian cotton fibers to remove (A) RBCs, (B) WBCs, (C) Plt, and (D) neutrophils and lymphocytes from whole blood.
Figure 18B:
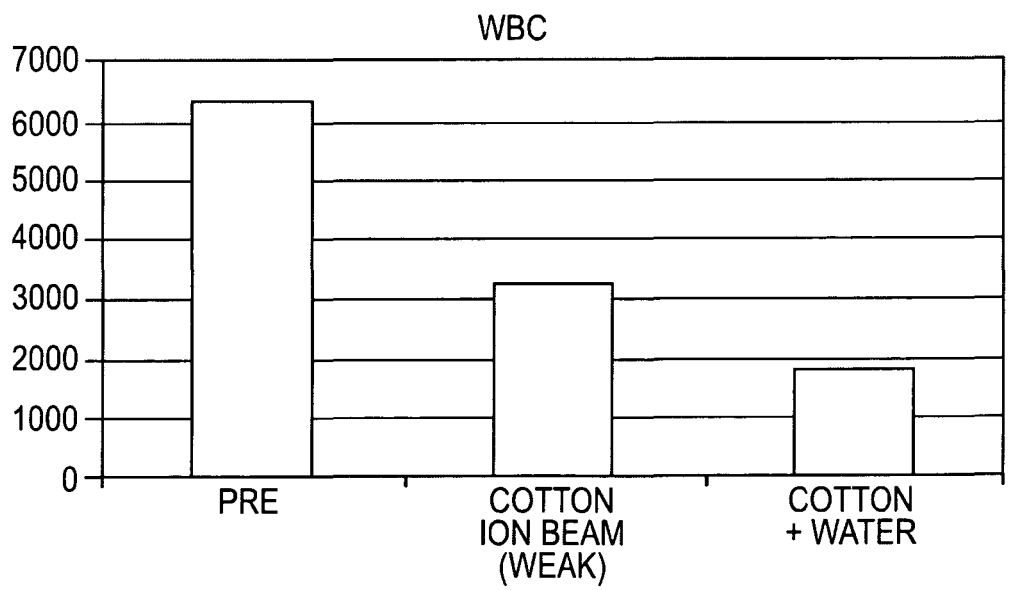
Figure 18C:
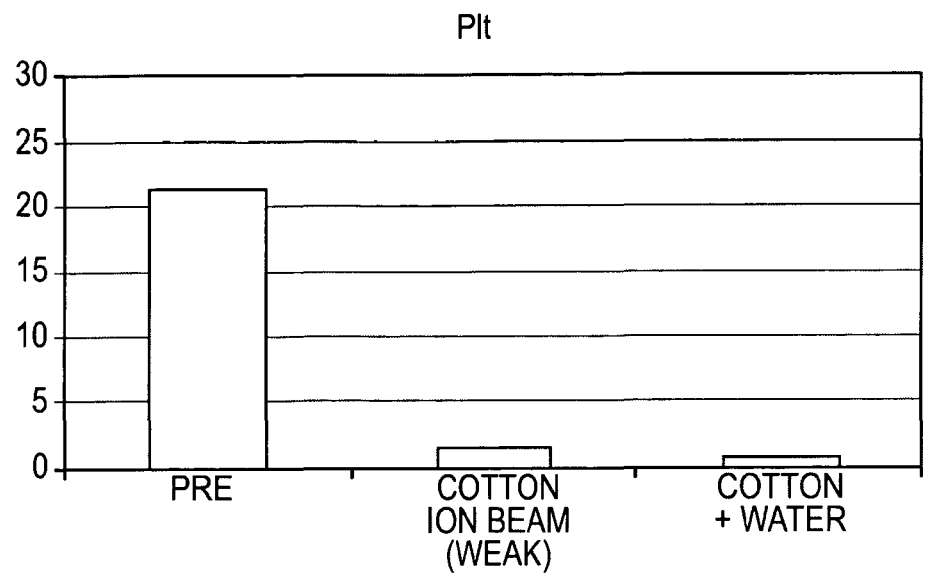
Figure 18D:
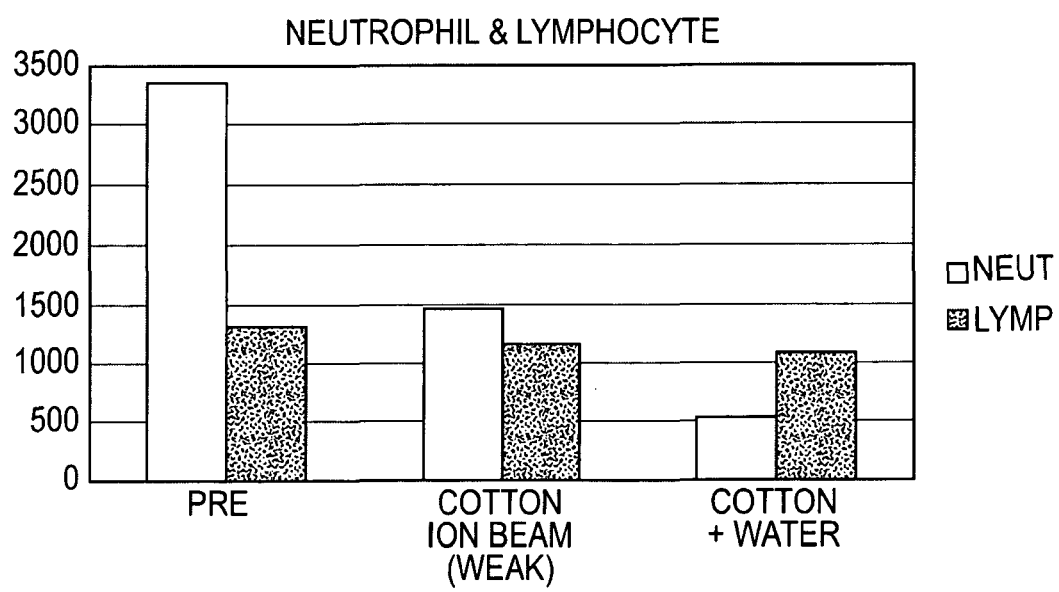
Figure 19A:
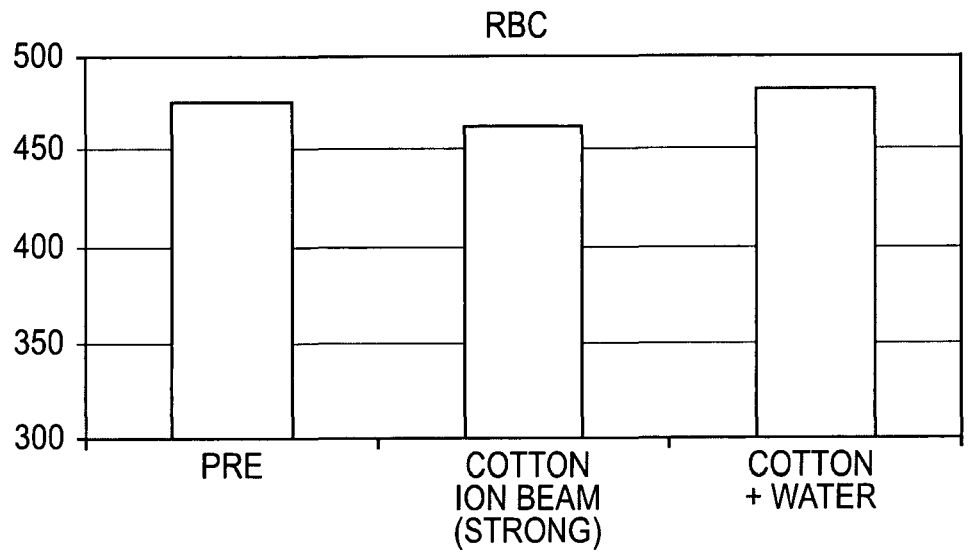
FIG. 19 shows the effect of biolization with strong ion-beam irradiation on the ability of Egyptian cotton fibers to remove (A) RBCs, (B) WBCs, (C) Plt, and (D) neutrophils and lymphocytes from whole blood.
Figure 19B:
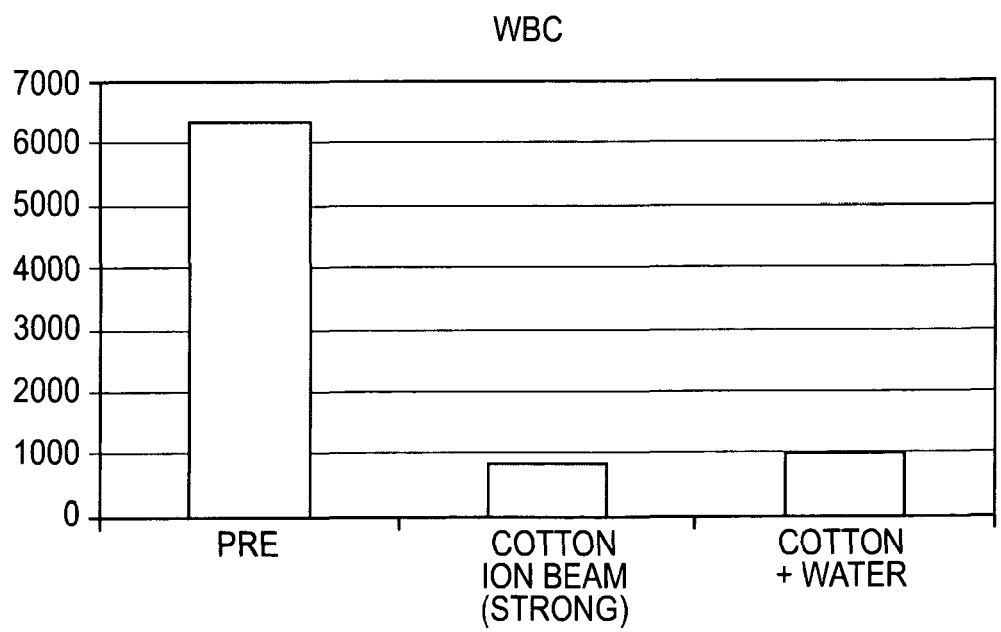
Figure 19C:
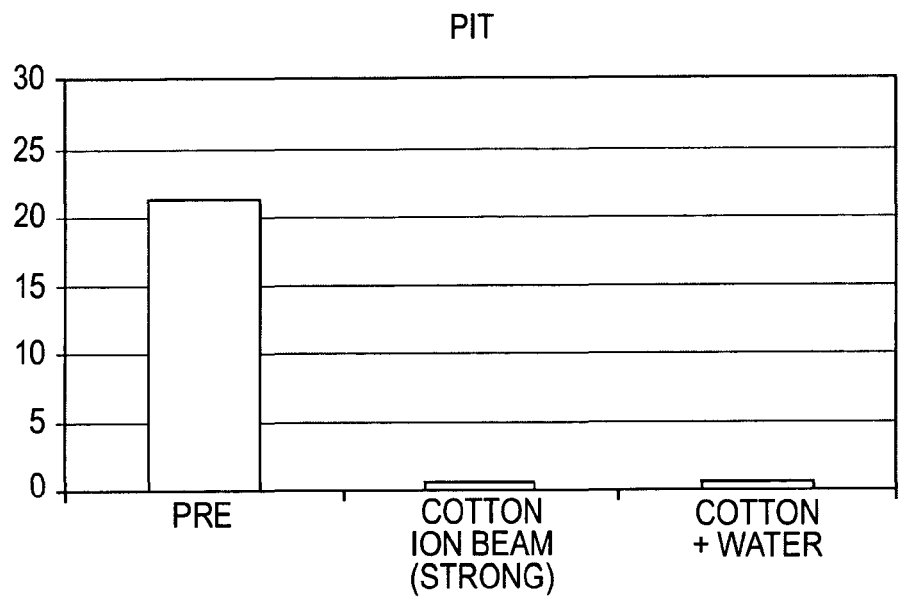
Figure 19D:
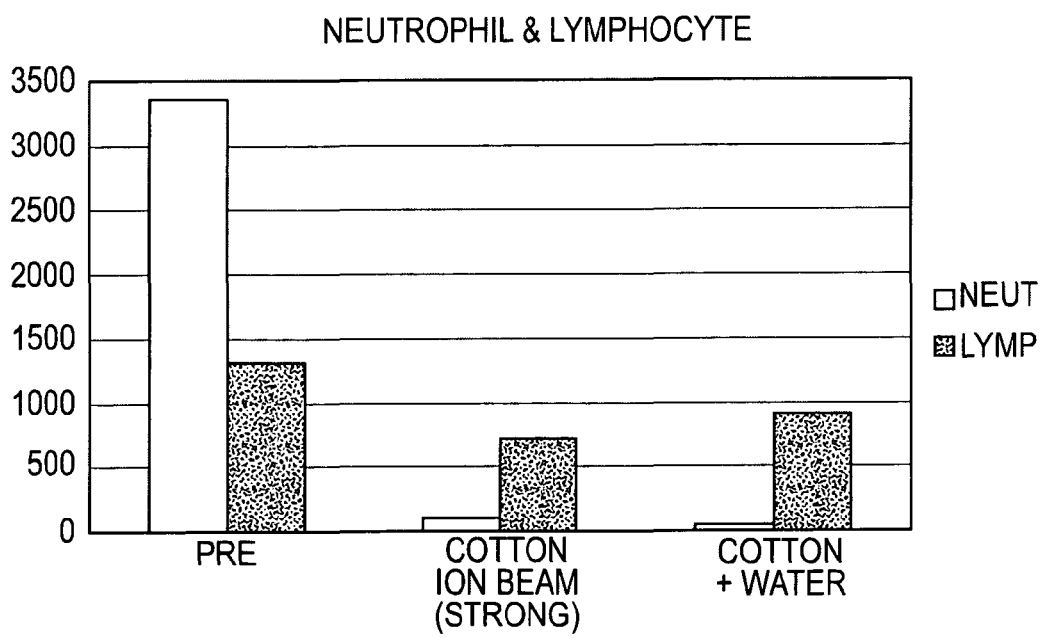

Biolization of Egyptian cotton by irradiation instead of chemical treatment was also tested. Cotton fibers were irradiated using an argon plasma based ion implantation device set at 5 kilovolts for either 0.5 hours (FIG. 18) or 1 hour (FIG. 19) before being prepared with saline as described above. Irradiation for 1 hour worked better than irradiation for 0.5 hours to filter out granulocytes. Based on this data, plasma based ion incorporation could be used to regulate the proportion of neutrophils that are removed from the blood. Compare neutrophil counts in FIGS. 18D and 19D.

Example 2

Immunoactivation in Mongrel Dogs

Figure 5B:
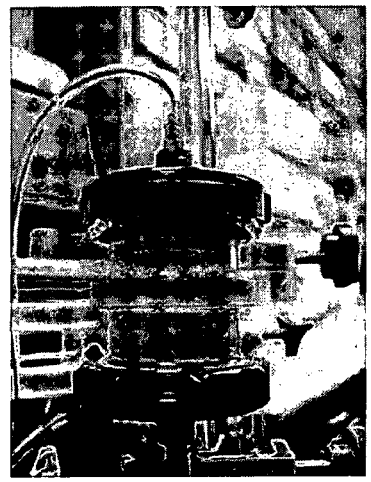
FIG. 5B is a photograph of an embodiment of the column.
Figure 6:
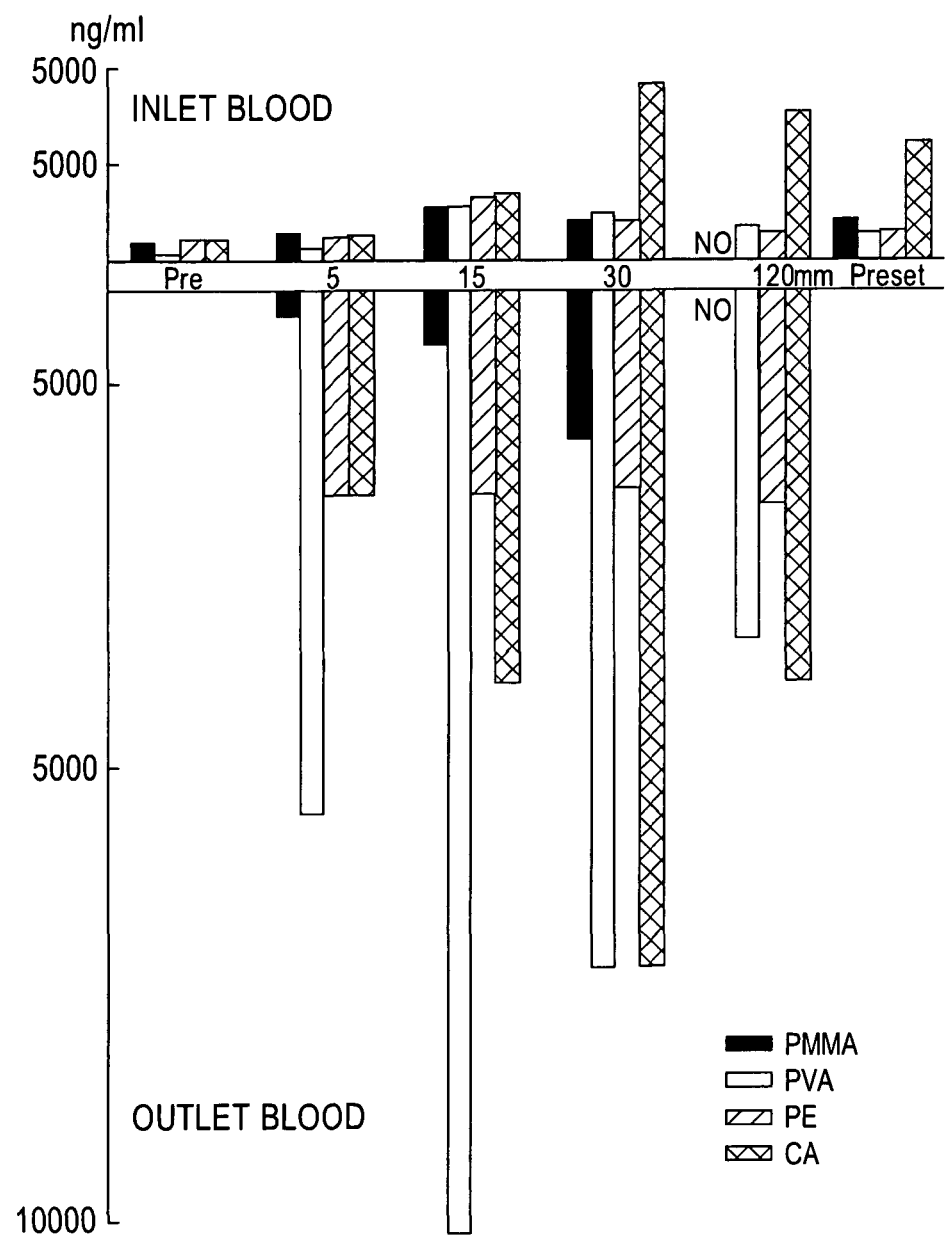
FIG. 6 shows the effect of apheresis on complement activation, as measured by factor $C_{3a}$ in inlet blood and outlet blood, over time using the following bioincompatible materials: polyethylene (PE), polymethylmethacrylate (PMMA), polyvinyl alcohol (PVA), and cellulose acetate (CA).

Six normal male mongrel dogs of 20-30 kg were subjected to apheresis experiments using a bioincompatible apheresis column containing natural non-synthetic non-plant fibers (ACS-A1 naturally obtained fibers of 1-2 µm in diameter) provided by Marubeni International Inc. Houston, Tex. See FIG. 5B. The column contained five grams of biolized ACS fibers These fibers were an effective leukocyte filter but, still functioned as a bioincompatible material. Five grams total of such fibers were incorporated inside of the column. Specifically, one gram of well washed fibers was contained in a separated chamber and was supported by non-woven PVA (polyethylene vinyl alcohol) provided by Kuraray Inc, Houston, Tex. at the top and bottom of the chamber to make a filtration unit. See FIG. 5A. Five filtration units were incorporated inside of the column.

Fibers were prepared by successive treatments with 0.5 N NaOH, 0.5 N HCl, 70% isopropyl alcohol. The fibers spent approximately 30 minutes in each solution with a rinsing step with water between solutions. The cartridge was washed and biolized by running a 10% formaldehyde solution through the column for 48 hours. Before the experiment, the processed fibers were packed into the column and then the blood circuit was set up.

The blood circuit comprised a roller pump, a tubing set, a heating unit, and an apheresis column. Before the start of an experiment the blood circuit was rinsed by normal saline until the residual formaldehyde concentration in rinsed solution became less than 5 ppm. The blood flow rate through the column was set at 3 ml/kg. Pressures of the inlet and outlet of the column were measured by the pressure gauges.

The apheresis column was connected to the dogs to complete the entire circuit of the extracorporeal circulation by PVC (polyvinyl chloride) tubing together with a warmer bag and an air removal chamber. The extracorporeal apheresis column was disinfected by 4% formaldehyde overnight, while the rest of the circuit components were previously sterilized prior to use.

Prior to extracorporeal apheresis, the dogs were anesthetized using a combination of Xylazin intramuscularly and Ketamine intramuscularly for induction of anesthesia followed by 2.5% isoflurane gas for maintenance. 3 L of oxygen, 5 L of air 2% isoflurane were added to the repiratory gas. As alternative anesthetic induction, Atropine was used. General anesthesia was administered within 60 minutes of beginning the apheresis treatment.

The dogs' blood was heparanized by initially administering a 200 unit/kg bolus intravenously and then during apheresis, the dogs continued to receive 100 units/kg of heparain and then the dogs' blood circulated through the apheresis column for one hour at a flow rate of 3.3 ml/kg as noted above. Following the one hour of apheresis, the dogs remained under general anesthesia for an additional five hours, making a total duration of six hours of general anesthesia from the time that extracorporeal apheresis began.

Figure 20A:
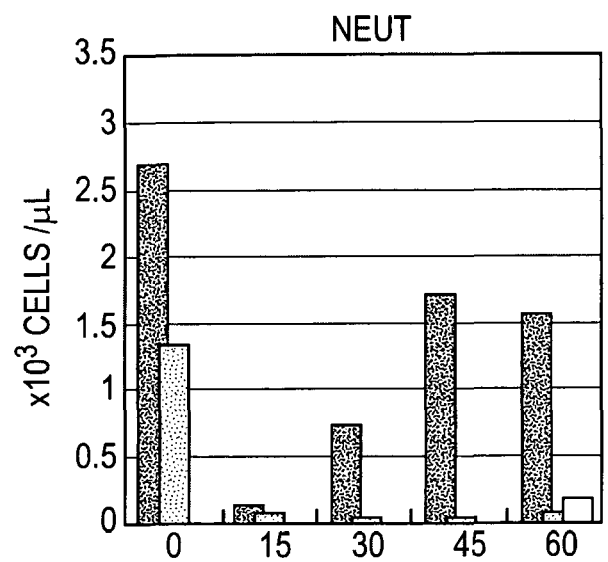
FIG. 20 shows the leukocytes analysis of pre and post perfusion of the blood. (A) neutrophils and (B) lymphocytes.
Figure 20B:
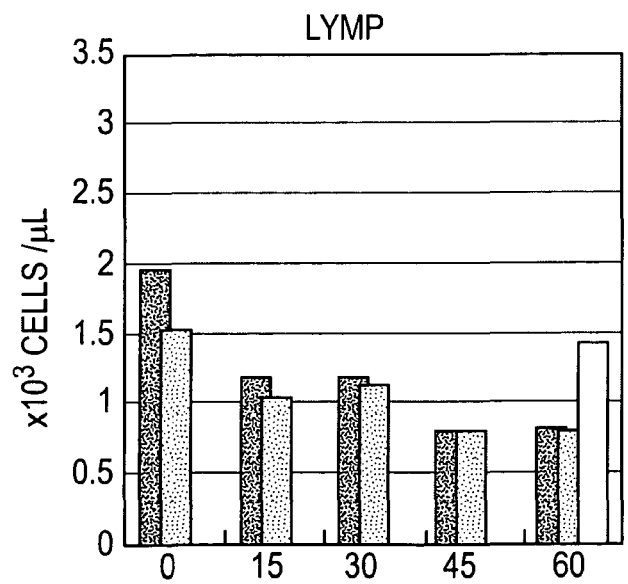

As shown in FIG. 20, this treatment resulted in ex vivo removal of leukocytes. In this Figure, the darkest bar indicated the leukocytes (represented by neutrophils and lymphocytes in this figure) present in the inlet blood, the blood that was traveling into the apheresis column. The medium colored bar represents the number of leukocytes present in the blood exiting the apheresis column and traveling back into the dog. The lightest colored bar represents the number of leukocytes present in the residual blood trapped inside the column. Almost all granulocytes were removed while only 60% of lymphocytes were removed, thus resulting in a lymphocyte-dominant state in the dogs.

Figure 21:
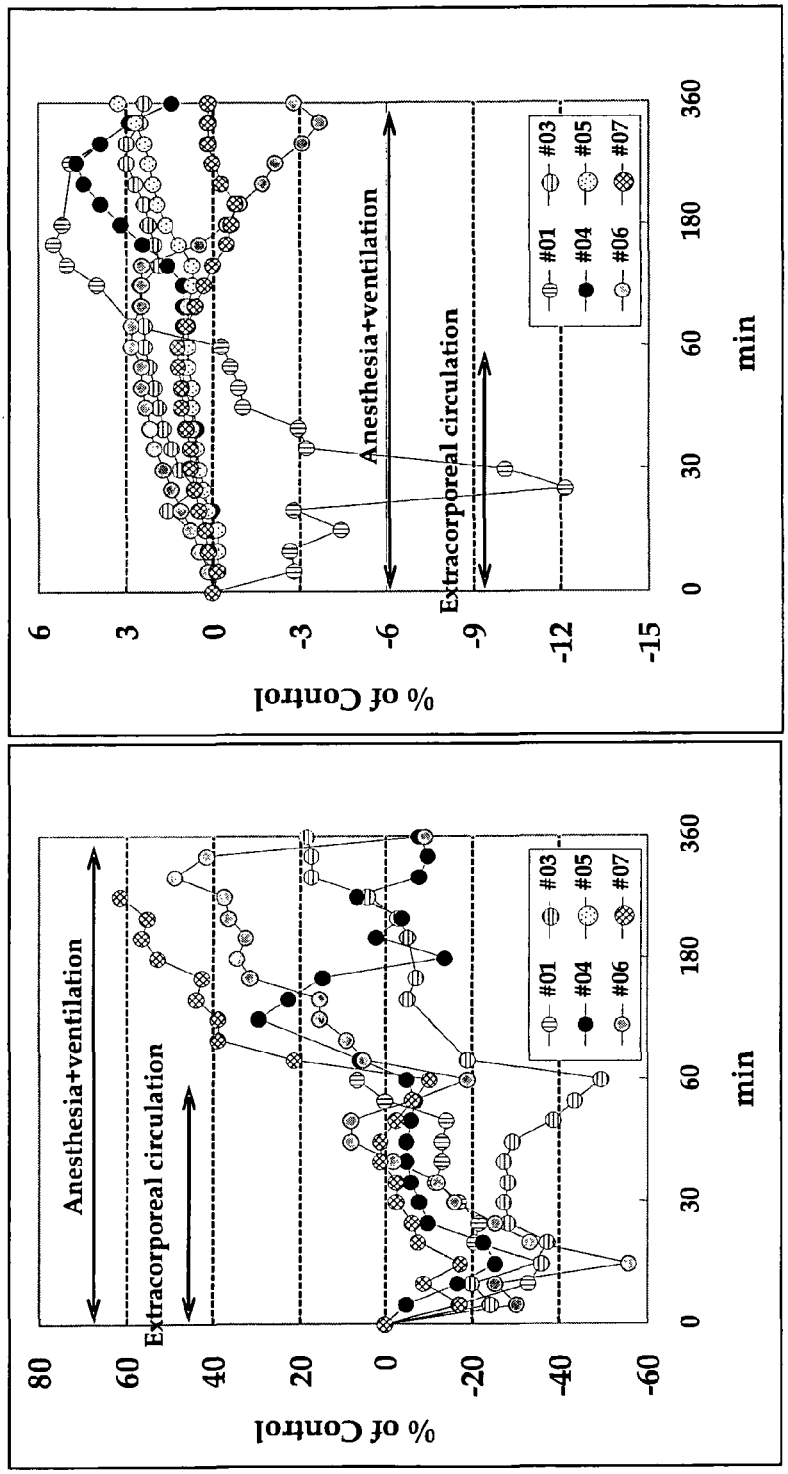
FIG. 21 shows the blood pressure and body temperature of dogs undergoing 6 hours of perfusion according to one embodiment of the invention.

As shown in FIG. 21, blood pressures had a tendency to drop transiently approximately 30 minutes after the onset of the apheresis. However, the blood pressure later increased after these transient drops. During anesthesia, blood gases were maintained while body temperatures tended to increase during the six hours of general anesthesia.

Figure 22:
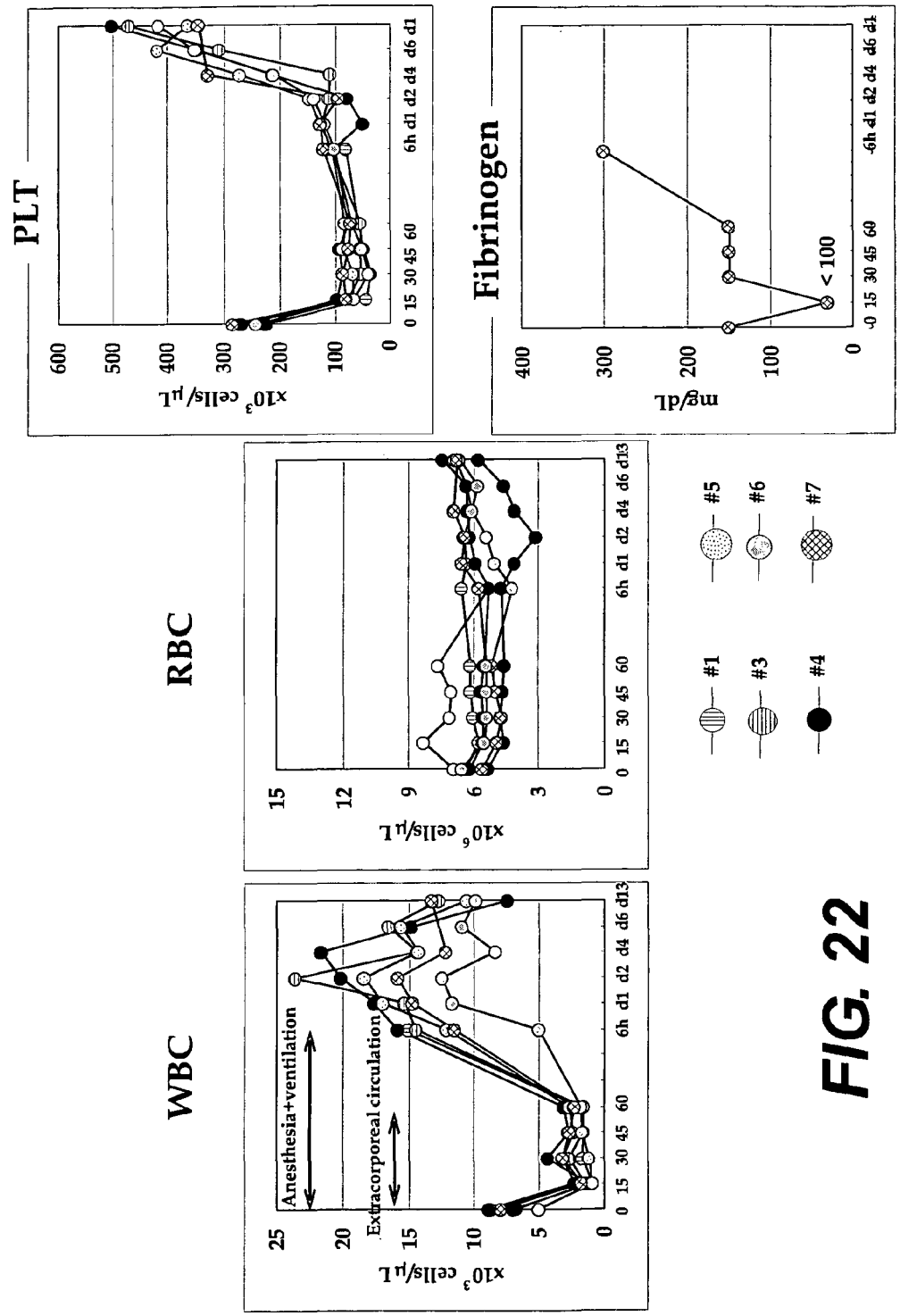
FIG. 22 shows the levels of WBCs, RBCs, Plt, and fibrinogen in dogs during and after perfusion according to one embodiment of the invention.

FIG. 22 shows that WBC counts and fibrinogen levels initially decreased during perfusion, but later recovered within hours of apheresis. Platelet counts, however, also dropped during apheresis and remained at relatively low numbers for approximately four days. RBC counts stayed fairly constant during and after the one hour apheresis treatment.

Figures 24A, 24B, 24C:
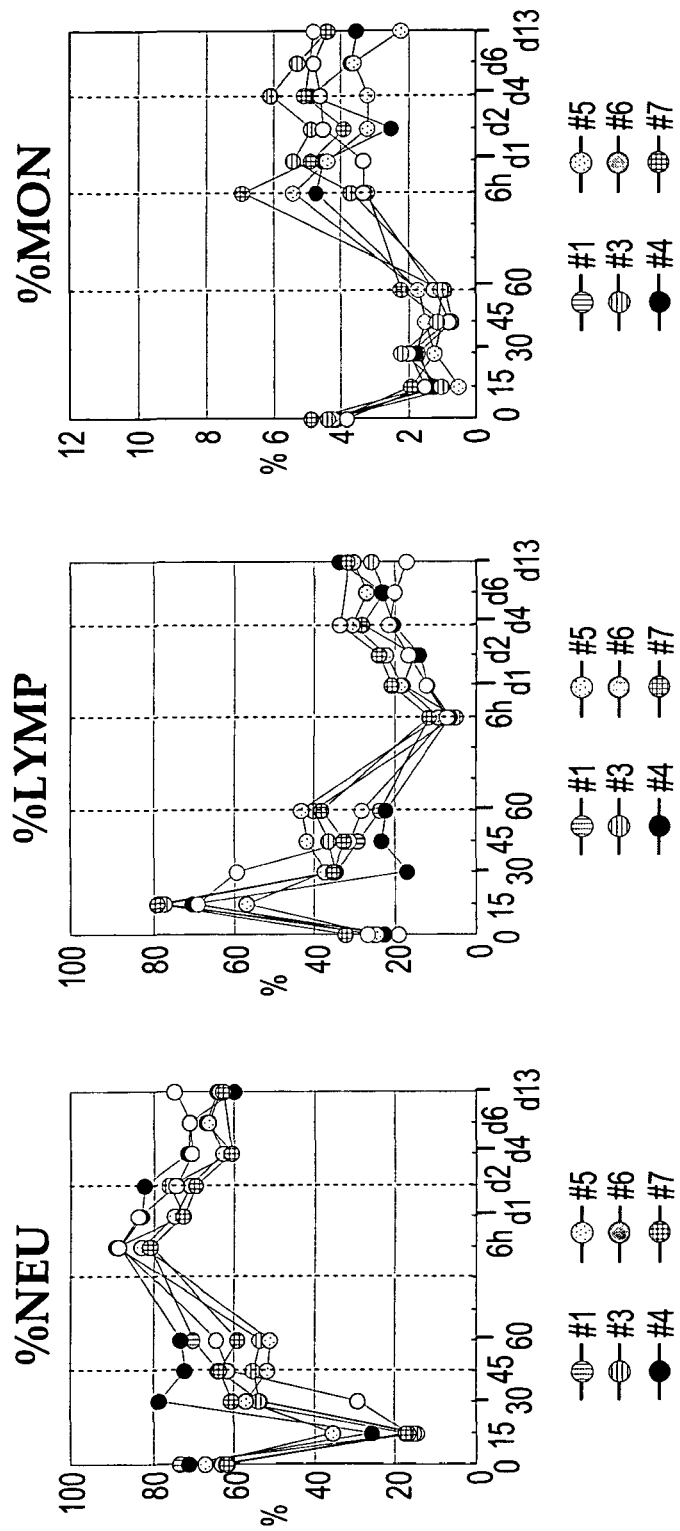
FIG. 24 shows the kinetics of lymphocyte, neutrophil, and monocyte recovery in dogs during and after perfusion according to one embodiment of the invention. The Y axis indicates the presence of each cell type as a percentage of total cells in the dogs' whole blood at each time point.

Granulocytes returned to circulation within the framework of 6 hours together with monocytes (FIG. 23), while lymphocytes remained reduced (FIG. 23B) during these six hours. In the short term, however, a transient state of lymphocyte dominance was established in the dogs. Specifically, the percentage of granulocytes and percentage of lymphocytes in the dogs' blood changed after 15 minutes of extracorporeal circulation. The percentage of neutrophils in the dogs' blood was only 20% while lymphocytes constituted 80% of the WBCs in the blood. In later time points, the percentage of neutrophils and monocytes returned to preoperative levels after 6 hours, but the percentage of lymphocytes remained low for 6 hours to 4 days after treatment (FIG. 24).

Figures 25A, 25B:
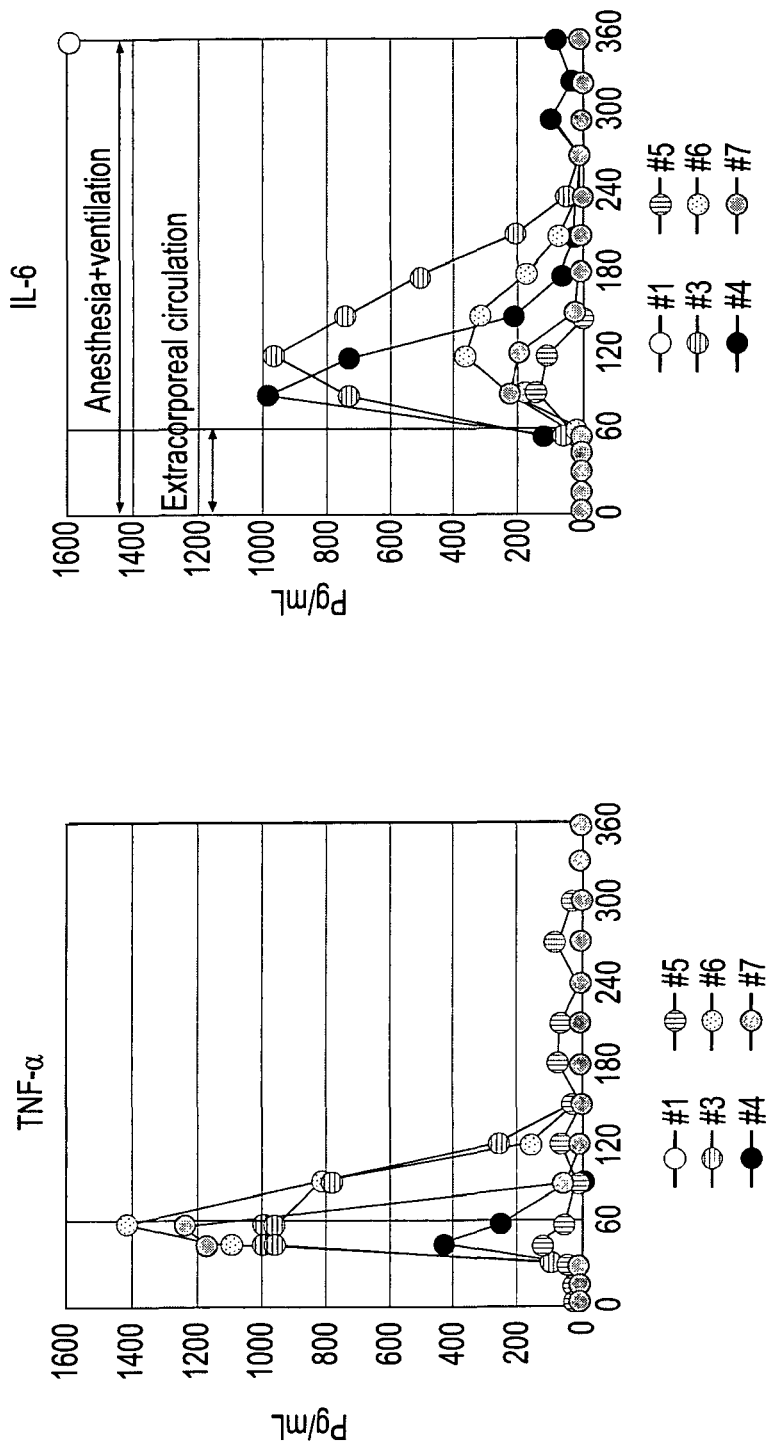
FIG. 25 shows the levels of tumor necrosis factor alpha (TNFα) and interleukin 6 (IL-6) in the blood of dogs during and after perfusion according to one embodiment of the invention. The Y axis measures the amount of cytokine present in picograms per milliliter, while the X axis represents minutes after the start of perfusion.

In addition to the transient lymphocyte dominant state of the dogs' immune system as a result of extracorporeal apheresis, there was also a transient increase in TNF-α of about 1,000 fold during the 30 to 90 minutes after apheresis began (FIG. 25). There was also a transient increase in IL-6 of about 1,000 fold during the 60 to 200 minutes after apheresis began (FIG. 25). In contrast, interferon gamma (IFN-γ) and interleukin 2 (IL-2) remained unchanged as did antibody levels during the two weeks following treatment.

The immunological shock associated with apheresis using bioincompatible materials includes dizziness due to hypotension, respiratory difficulty, nausea and vomiting, excessive sweating, fever, chills, and shivers. To safely manage these physiological effects, the method of the invention is performed under general anesthesia. By doing so, the patient can undergo reproducible and effective immunoactivation apheresis therapy for the treatment of malignant tumors and infectious diseases. Unsafe and dangerous shock inducing immunoactivation apheresis therapy now becomes a safe, effective, and painless therapeutic molecular surgical procedure because of the invention.

In one embodiment, the effective and safe immunoactivation therapy of the invention can be described in the following eight features: (1) general anesthesia with intra-tracheal intubation; (2) careful monitoring of blood pressure and arterial blood oxygen contents; (3) sufficient supply of oxygen; (4) careful flow controls during extracorporeal circulation and automatic blood flow reduction whenever hypotension and hypoxia should occur more than expected levels; (5) extracorporeal circulation lasting approximately 60 minutes or less; (6) maintenance of intratracheal anesthesia for at least six hours, during which the patient receives physiological support while under general anesthesia; (7) after four days of immunoactivation, transient increase in leukocytes counts occur; and (8) follow up monitoring of cellular and humoral immunological responses for two weeks after completion of the apheresis treatment.

It was possible to produce an immunological active state of the patient by subjecting the patient for one hour to an apheresis procedure with bioincompatible biomaterials. The induced immunoactive state of the patient would then lead to apoptosis of tumor cells or infected cells without any harm to natural, healthy cells of the patient.

Cited References

Ainsworth S. K., et al. Toxicity following protein A treatment of Metastic breast adenocarcinoma cancer 61:1495-1500, 1988.

Amano K. et al. Filter leucopheresis for patients with ulcerative colitis; clinical results and the possible mechanism. Therapeutic Apheresis 2(2) 97-100, 1998.

Amano K. et al., Four year study of Leukapheresis with *Gossypium barbadense* cotton for Rheumatoid Arthritis Japanese Journal for Apheresis 15(1) 103-104, 1996.

Grange J. M. et al., Immunotherapy for malignant melanomia—Tracing Ariadne's thread through the labyrinth, European Journal of Cancer 45(13), 2266-73, 2009.

Levy J. et al., Correcting immune imbalance: The use of prosorba column treatment for immune disorders. Therapeutic Apheresis and Dialysis 7(2) 197-203. 2003.

Messerschmidt G. L. et al., Protein A immunoadsorption in the treatment of malignant disease J. Clinical Oncology (12) 203-212,1988.

Nosé Y., et al. Therapeutic Membrane Plasmapheresis. Therapeutic apheresis 4(1) 3-9, 2000 (originally published in 1981).

Nosé Y. Blood purification procedures and their related short and long term effects on patients. Therapeutic apheresis 6(5), 333-347, 2002.

Nosé Y. Congress presidential address: 5th WAA congress, Therapeutic Artificial Organs: 10 years after, Artificial Organs 1995.

Tani, T. et al. Blood purification therapy in cancer treatment, Therapeutic apheresis 2(3) 182-184, 1998.

Yonekawa M., granulocyte removal therapy for cancer Tissue Culture Engineering [Japanese Text] 23(12) 481-485, 1997.

Yonekawa M. Granulocytapheresis in Cancer Tissue Culture Engineering (Japanese Text) 23 (12) 481-485, 1997.

Yonekawa M., Kamii N., Onodera K. et al Basic Study of Extracorporeal Granulocyte/Lymphocyte Regulation System Therapeutic Plasmapheresis (X) ICAOT Press, Cleveland pp. 37-42, 1992.

We claim:

1. A method of treating a disease in a patient comprising:
   (a) providing an apheresis system including a blood perfusion filter comprising at least one bioincompatible material;
   (b) connecting the patient's blood circulation with the apheresis system such that the patient's blood passes through the blood perfusion filter before reentering the patient's body;
   (c) placing the patient under general anesthesia and providing physiological support to the patient;
   (d) circulating the patient's blood through the apheresis system for about one hour; and
   (e) keeping the patient under general anesthesia for at least 5 hours after circulating the patient's blood through the apheresis system,
   wherein circulating the patient's blood through the blood perfusion filter creates a lymphocyte dominant state in the patient's immune system.

2. The method of claim 1, wherein the disease is a malignant tumor.

3. The method of claim 1, wherein the disease is an infectious disease.

4. The method of claim 3, wherein the infectious disease is acquired immune deficiency syndrome (AIDS) or hepatitis.

5. The method of claim 1, wherein the apheresis system further comprises an air chamber and/or a warming bag.

6. The method of claim 1, wherein the bioincompatible material is a cotton or a silk.

7. The method of claim 6, wherein the cotton is selected from Egyptian cotton, Australian cotton, and Pakistani cotton.

8. The method of claim 6, wherein the silk is selected from Japanese silk and Kanton silk.

9. The method of claim 1, wherein the bioincompatible material is biolized.

10. The method of claim 9, wherein the bioincompatible material is biolized with formaldehyde or glutaraldehyde.

11. The method of claim 1, wherein the patient is a human patient.

12. The method of claim 1, wherein the patient is a non-human animal.

13. The method of claim 1, wherein the general anesthesia is ketamine.

14. The method of claim 1, wherein the physiological support is chosen from at least one of maintenance of blood pressure and maintenance of blood gas levels.

15. The method of claim 1, further comprising the step of administering an anticoagulant to the patient before circulating the patient's blood through the apheresis system.

16. The method of claim 15, wherein the anticoagulant is heparin.

17. The method of claim 1, wherein the patient's blood is circulated through the apheresis system at a rate of about 100 to 200 ml/minute.

18. A method of treating a disease in a patient comprising:
   (a) connecting an apheresis system including a blood perfusion filter comprising at least one bioincompatible material to a patient's blood circulation such that the patient's blood can pass through the blood perfusion filter before reentering the patient's body; and
   (b) administering a general anesthetic for anesthetizing the patient during use of the apheresis system and for at least 5 hours following that use for treating a disease in a patient,
   wherein use of the apheresis system creates a lymphocyte dominant state in the patient's immune system.

19. A kit for treating a disease in a patient comprising:
   (a) an apheresis system including a blood perfusion filter comprising at least one bioincompatible material, and
   (b) a general anesthetic for anesthetizing the patient during use of the apheresis system and for at least 5 hours following that use for treating a disease in a patient,
   wherein use of the apheresis system creates a lymphocyte dominant state in the patient's immune system.

* * * * *